(12) United States Patent
Wren et al.

(10) Patent No.: US 10,646,562 B2
(45) Date of Patent: *May 12, 2020

(54) GLYCOSYLATION METHOD

(71) Applicant: London School of Hygiene and Tropical Medicine, London (GB)

(72) Inventors: Brendan Wren, London (GB); Jon Cuccui, London (GB); Sherif Abouelhadid, London (GB)

(73) Assignee: London School of Hygiene and Tropical Medicine, London (GB)

( * ) Notice: Subject to any disclaimer, the term of this patent is extended or adjusted under 35 U.S.C. 154(b) by 151 days.

This patent is subject to a terminal disclaimer.

(21) Appl. No.: 15/892,624

(22) Filed: Feb. 9, 2018

(65) Prior Publication Data

US 2018/0169212 A1   Jun. 21, 2018

Related U.S. Application Data

(63) Continuation of application No. 14/655,128, filed as application No. PCT/GB2014/050133 on Jan. 17, 2014, now Pat. No. 9,931,392.

(51) Int. Cl.

| | | |
|---|---|---|
| *C12N 9/10* | (2006.01) | |
| *C12P 21/00* | (2006.01) | |
| *A61K 39/02* | (2006.01) | |
| *C12N 15/70* | (2006.01) | |
| *C12N 15/74* | (2006.01) | |
| *C12N 1/20* | (2006.01) | |
| *A61K 39/09* | (2006.01) | |

(52) U.S. Cl.
CPC .......... *A61K 39/105* (2013.01); *A61K 39/092* (2013.01); *C12N 1/20* (2013.01); *C12N 9/1048* (2013.01); *C12N 15/70* (2013.01); *C12N 15/74* (2013.01); *C12P 21/005* (2013.01)

(58) Field of Classification Search
None
See application file for complete search history.

(56) References Cited

U.S. PATENT DOCUMENTS

| | | | |
|---|---|---|---|
| 9,642,902 B2 | 5/2017 | Wren et al. | |
| 9,931,392 B2 * | 4/2018 | Wren | C12P 21/005 |
| 2003/0013175 A1 | 1/2003 | Koizumi et al. | |
| 2010/0062484 A1 | 3/2010 | Aebi et al. | |
| 2010/0137565 A1 | 6/2010 | Javaud et al. | |
| 2011/0274720 A1 | 11/2011 | Wacker et al. | |

(Continued)

FOREIGN PATENT DOCUMENTS

| | | |
|---|---|---|
| JP | 2005-046031 A | 2/2005 |
| WO | WO 1999/54342 A1 | 10/1999 |

(Continued)

OTHER PUBLICATIONS

U.S. Appl. No. 14/655,128, filed Jun. 24, 2015.

(Continued)

*Primary Examiner* — Richard C Ekstrom
(74) *Attorney, Agent, or Firm* — Klarquist Sparkman, LLP

(57) ABSTRACT

The invention relates to microbial host cells engineered to produce glycoconjugate vaccines by stable integration of an acceptor protein and an oligosaccharyltransferase into the host's genome, wherein expression of the oligosaccharyltransferase is regulated.

27 Claims, 7 Drawing Sheets

Specification includes a Sequence Listing.

(56) References Cited

U.S. PATENT DOCUMENTS

| | | | |
|---|---|---|---|
| 2015/0328301 A1 | 11/2015 | Wren et al. | |
| 2015/0344928 A1 | 12/2015 | Wren et al. | |
| 2017/0196958 A1 | 7/2017 | Wren et al. | |
| 2018/0169212 A1* | 6/2018 | Wren | C12P 21/005 |

FOREIGN PATENT DOCUMENTS

| | | |
|---|---|---|
| WO | WO 2003/102191 A1 | 12/2003 |
| WO | WO 2007/035897 A2 | 3/2007 |
| WO | WO 2008/021076 A2 | 2/2008 |
| WO | WO 2008/133645 A2 | 11/2008 |
| WO | WO 2009/026131 A2 | 2/2009 |
| WO | WO 2009/104074 A2 | 8/2009 |
| WO | WO 2011/027116 A1 | 3/2011 |
| WO | WO 2011/115483 A1 | 9/2011 |
| WO | WO 2011/138361 A1 | 11/2011 |
| WO | WO 2012/158701 A1 | 11/2012 |

OTHER PUBLICATIONS

U.S. Appl. No. 14/655,210, filed Jun. 24, 2015.
U.S. Appl. No. 15/465,312, filed Mar. 21, 2017.
Conlan et al., "Mice Vaccinated with the O-antigen of *Francisella tularensis* LVS Lipopolysaccharide Conjugated to Bovine Serum Albumin Develop Varying Degrees of Protective Immunity Against Systemic or Aerosol Challenge with Virulent type A and Type B Strains of the Pathogen," *Vaccine* 20:3465-3471, 2002.
Cuccui et al., "Exploitation of Bacterial N-linked Glycosylation to Develop a Novel Recombinant Glycoconjugate Vaccine Against *Francisella tularensis*," *Open Biol.* 3:130002, 2013.
Dagan et al., "Glycoconjugate Vaccines and Immune Interference: A Review," *Vaccine* 28:5513-5523, 2010.
Feldman et al., "Engineering N-linked Protein Glycosylation with Diverse O Antigen Lipopolysaccharide Structures in *Escherichia coli*," *Proc Natl Acad Sci. USA* 102:3016-3021, 2005.
Guo et al., "Protein tolerance to random amino acid change," *Proc Natl Acad Sci. USA* 101:9205-9210, 2004.
Ihssen et al., "Production of Glycoprotein Vaccines in *Escherichia coli*," *Microbiol. Cell Factories* 9:61, 2010.
Kim et al., "Genetic Modification of the O-Polysaccharide of *Francisella tularensis* Results in an Avirulent Live Attenuated Vaccine," *J Infect Dis.* 205:1056-1065, 2012.
Kowarik et al., "N-Linked Glycosylation of Folded Proteins by the Bacterial Oligosaccharyltransferase," *Science* 314:1148-1150, 2006.
Nikel and Lorenzo, "Implantation of Unmarked Regulatory and Metabolic Modules in Gram-Negative Bacteria with Specialised Mini-Transposon Delivery Vectors," *J Biotechnol.* 163:143-154, 2013.
Prior et al., "Characterization of the O Antigen Gene Cluster and Structural Analysis of the O Antigen of *Francisella tularensis* subsp. *tularensis*," *J Med Microbiol.* 52:845-851, 2003.
Sabido et al., "A Novel Plasmid Vector Designed for Chromosomal Gene Integration and Expression: Use for Developing a Genetically Stable *Escherichia coli* Melanin Production Strain," *Plasmid* 69:16-23, 2013.
Terra et al., "Recent Developments in Bacterial Protein Glycan Coupling Technology and Glycoconjugate Vaccine Design," *J Med Microbiol.* 61:919-926, 2012.
Great Britain Search Report dated Jul. 18, 2013 for Great Britain Application No. GB1300956.8.
Great Britain Search Report dated Jul. 16, 2013 for Great Britain Application No. GB1301085.5.

\* cited by examiner

FIG. 3A (SEQ ID NO: 1)

ATGTTGAAAAAAGAGTATTTAAAAAACCCTTATTTAGTTTTGTTTGCGATGATTATATTA
GCTTATGTTTTAGTGTATTTTGCAGGTTTTATTGGGTTTGGTGGGCAAGTGAGTTTAAT
GAGTATTTTTTCAATAATCAGTTAATGATCATTTCAAATGATGGCTATGCTTTTGCTGAG
GGCGCAAGAGATATGATAGCAGGTTTTCATCAGCCTAATGATTGAGTTATTATGGATCT
TCTTTATCCGCGCTTACTTATTGGCTTTATAAAATCACACCTTTTTCTTTTGAAAGTATC
ATTTTATATGAGTACTTTTTATCTTCTTTGGTGGTGATTCCTACTATTTGCTAGCT
AACGAATACAAACGTCCTTTAATGGGCTTTGTAGCTGCTCTTTTAGCAAGTATAGCAAAC
AGTTATTATAATCGCACTATGAGTGGGTATTATGATACGGATATGCTGGTAATTGTTTTG
CCTATGTTTATTTTATTTTTATGGTAAGAATGATTTTAAAAAAGACTTTTTTCATTG
ATTGCCTTGCCGTTATTTATAGGAATTTATCTTTGGTGGTATCCTTCAAGTTATACTTTA
AATGTAGCTTTAATTGGACTTTTTTAATTTATACACTTATTTTTCATAGAAAAGAAAAG
ATTTTTTATATAGCTGTGATTTGTCTTCTCTTACTCTTTCAAATATAGCATGGTTTTAT
CAAAGTGCCATTATAGTAATACTTTTGCTTTATTCGCCTTAGAGCAAAAACGCTTAAAT
TTATGATTATAGGAATTTTAGGTAGTGCAACTTTGATATTTTGATTTAAGTGGTGGG
GTTGATCCTATACTTTATCAGCTTAAATTTATATTTTAGAAGTGATGAAAGTGCGAAT
TAACGCAGGGCTTTATGTATTTAATGTCAATCAAACCATACAAGAAGTTGAAAATGTA
GATCTTAGCGAATTTATGCGAAGAATTAGTGGTAGTGAAATTGTTTTTTGTTTCTTTG
TTTGGTTTTGTATGGCTTTTGAGAAAACATAAAAGTATGATTATGGCTTTACCTATATTG
GTGCTTGGGTTTTAGCCTTAAAAGGGGGCTTAGATTTACCATTTATTCTGTACCTGTA
ATGGCCTTAGGATTTGGTTTTTATTGAGCGAGTTTAAGGCTATAATGGTTAAAAATAT
AGCCAATTAACTTCAAATGTTTGTATTGTTTTGCAACTATTTTGACTTTAGCTCCAGTA
TTTATCCATATTTACAACTATAAAGCGCCAACAGTTTTTTCTCAAAATGAAGCATCATTA
TTAAATCAATTAAAAAATATAGCCAATAGAGAAGATTATGTGGTAACTTGGTGGGATTAT
GGTTATCCTGTGCGTTATTATAGCGATGTGAAAACTTTAGTAGATGGTGGAAAGCATTTA
GGTAAGGATAATTTTTTCCCTTCTTTTGCTTTAAGCAAAGATGAACAAGCTGCAGCTAAT
ATGGCAAGACTTAGTGTAGAATATACAGAAAAAGCTTTTATGCTCCGCAAAATGATATT
TTAAAAACAGACATTTTGCAAGCCATGATGAAAGATTATAATCAAAGCAATGTGGATTTG
TTTCTAGCTTCATTATCAAAACCTGATTTTAAAATCGATACGCCAAAAACTCGTGATATT
TATCTTTATATGCCCGCTAGAATGTCTTTGATTTTTCTACGGTGGCTAGTTTTCTTTT
ATTAATTTAGATACAGGAGTTTTGGATAAACCTTTTACCTTTAGCACAGCTTATCCACTT
GATGTTAAAAATGGAGAAATTTATCTTAGCAACGGAGTGGTTTAAGCGATGATTTAGA
AGTTTTAAAATAGGTGATAATGTGGTTTCTGTAAATAGTATCGTAGAGATTAATTCTATT
AAACAAGGTGAATACAAAATCACTCCAATTGATGATAAGGCTCAGTTTATATTTTTAT
TTAAAGGATAGTGCTATTCCTTACGCACAATTTATTTAATGGATAAAACCATGTTTAAT
AGTGCTTATGTGCAAATGTTTTTTTAGGAAATTATGATAAGAATTTATTTGACTTGGTG
ATTAATTCTAGAGATGCTAAGGTTTTTAAACTTAAAATTTAA

FIG. 3B (SEQ ID 2)

MLKKEYLKNPYLVLFAMIILAYVFSVFCRFYWVWWASEFNEYFFNNQLMIISNDGYAFAEGARDM
IAGFHQPNDLSYYGSSLSALTYWLYKITPFSFESIILYMSTFLSSLVVIPTILLANEYKRPLMGF
VAALLASIANSYYNRTMSGYYDTDMLVIVLPMFILFFMVRMILKKDFFSLIALPLFIGIYLWWYP
SSYTLNVALIGLFLIYTLIFHRKEKIFYIAVILSSLTLSNIAWFYQSAIIVILFALFALEQKRLN
FMIIGILGSATLIFLILSGGVDPILYQLKFYIFRSDESANLTQGFMYFNVNQTIQEVENVDLSEF
MRRISGSEIVFLFSLFGFVWLLRKHKSMIMALPILVLGFLALKGGLRFTIYSVPVMALGFGFLLS
EFKAIMVKKYSQLTSNVCIVFATILTLAPVFIHIYNYKAPTVFSQNEASLLNQLKNIANREDYVV
TWWDYGYPVRYYSDVKTLVDGGKHLGKDNFFPSFALSKDEQAAANMARLSVEYTEKSFYAPQNDI
LKTDILQAMMKDYNQSNVDLFLASLSKPDFKIDTPKTRDIYLYMPARMSLIFSTVASFSFINLDT
GVLDKPFTFSTAYPLDVKNGEIYLSNGVVLSDDFRSFKIGDNVVSVNSIVEINSIKQGEYKITPI
DDKAQFYIFYLKDSAIPYAQFILMDKTMFNSAYVQMFFLGNYDKNLFDLVINSRDAKVFKLKI

FIG. 4 (SEQ ID 13)

5'ATGTCCAATTTACTGACCGTACACCAAAATTTGCCTGCATTACCGGTCGATGCAACGAGTGAT
GAGGTTCGCAAGAACCTGATGGACATGTTCAGGGATCGCCAGGCGTTTTCTGAGCATACCTGGAA
AATGCTTCTGTCCGTTTGCCGGTCGTGGGCGGCATGGTGCAAGTTGAATAACCGGAAATGGTTTC
CCGCAGAACCTGAAGATGTTCGCGATTATCTTCTATATCTTCAGGCGCGCGGTCTGGCAGTAAAA
ACTATCCAGCAACATTTGGGCCAGCTAAACATGCTTCATCGTCGGTCCGGGCTGCCACGACCAAG
TGACAGCAATGCTGTTTCACTGGTTATGCGGCGGATCCGAAAAGAAACGTTGATGCCGGTGAAC
GTGCAAAACAGGCTCTAGCGTTCGAACGCACTGATTTCGACCAGGTTCGTTCACTCATGGAAAAT
AGCGATCGCTGCCAGGATATACGTAATCTGGCATTTCTGGGGATTGCTTATAACACCCTGTTACG
TATAGCCGAAATTGCCAGGATCAGGGTTAAAGATATCTCACGTACTGACGGTGGGAGAATGTTAA
TCCATATTGGCAGAACGAAAACGCTGGTTAGCACCGCAGGTGTAGAGAAGGCACTTAGCCTGGGG
GTAACTAAACTGGTCGAGCGATGGATTTCCGTCTCTGGTGTAGCTGATGATCCGAATAACTACCT
GTTTTGCCGGGTCAGAAAAATGGTGTTGCCGCGCCATCTGCCACCAGCCAGCTATCAACTCGCG
CCCTGGAAGGGATTTTTGAAGCAACTCATCGATTGATTTACGGCGCTAAGGATGACTCTGGTCAG
AGATACCTGGCCTGGTCTGGACACAGTGCCCGTGTCGGAGCCGCGCGAGATATGGCCCGCGCTGG
AGTTTCAATACCGGAGATCATGCAAGCTGGTGGCTGGACCAATGTAAATATTGTCATGAACTATA
TCCGTAACCTGGATAGTGAAACAGGGGCAATGGTGCGCCTGCTGGAAGATGGCGATTAG-3'

FIG. 5 (SEQ ID 14)

5'ATGAGCCAGTTCGATATCCTGTGTAAAACCCCGCCTAAGGTGCTTGTTCGTCAGTTTGTGGAA
AGGTTTGAAAGACCTTCAGGTGAGAAAATAGCATCCTGTGCTGCTGAACTAACCTATTTATGTTG
GATGATTACACATAACGGAACAGCAATCAAGAGAGCCACATTCATGAGCTATAATACTATCATAA
GCAATTCGCTGAGTTTCGATATTGTCAATAAATCACTCCAGTTTAAATACAAGACGCAAAAAGCA
ACAATTCTGGAAGCCTCATTAAAGAAATTGATTCCTGCTTGGGAATTTACAATTATTCCTTACAA
CGGACAAAAACATCAATCTGATATCACTGATATTGTAAGTAGTTTGCAATTACAGTTCGAATCAT
CGGAAGAAGCAGATAAGGGAAATAGCCACAGTAAAAAAATGCTTAAAGCACTTCTAAGTGAGGGT
GAAAGCATCTGGGAGATCACTGAGAAATACTAAATTCGTTTGAGTATACTTCGAGATTTACAAA
AACAAAAACTTTATACCAATTCCTCTTCCTAGCTACTTTCATCAATTGTGGAAGATTCAGCGATA
TTAAGAACGTTGATCCGAAATCATTTAAATTAGTCCAAAATAAGTATCTGGGAGTAATAATCCAG
TGTTTAGTGACAGAGACAAAGACAAGCGTTAGTAGGCACATATACTTCTTTAGCGCAAGGGGTAG
GATCGATCCACTTGTATATTTGGATGAATTTTTGAGGAATTCTGAACCAGTCCTAAAACGAGTAA
ATAGGACCGGCAATTCTTCAAGCAATAAACAGGAATACCAATTATTAAAAGATAACTTAGTCAGA
TCGTACAATAAAGCTTTGAAGAAAATGCGCCTTATCCGATCTTTGCTATAAAAAATGGCCCAAA
ATCTCACATTGGAAGACATTTGATGACCTCATTTCTTTCAATGAAGGGCCTAACGGAGTTGACTA
ATGTTGTGGGAAATTGGAGCGATAAGCGTGCTTCTGCCGTGGCCAGGACAACGTATACTCATCAG
ATAACAGCAATACCTGATCACTACTTCGCACTAGTTTCTCGGTACTATGCATATGATCCAATATC
AAAGGAAATGATAGCATTGAAGGATGAGACTAATCCAATTGAGGAGTGGCAGCATATAGAACAGC
TAAAGGGTAGTGCTGAAGGAAGCATACGATACCCGCATGGAATGGGATAATATCACAGGAGGTA
CTAGACTACCTTTCATCCTACATAAATAGACGCATATAG-3'

FIG. 6

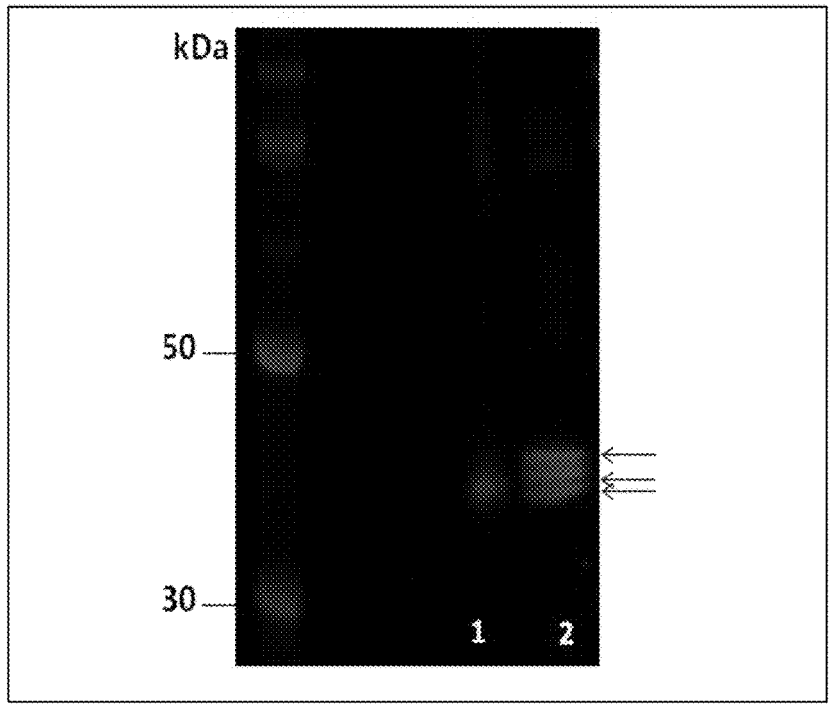

FIG. 9 (SEQ ID 22) Campylobacter sputorum

```
ATGTCAAATTTTAATTTCGCTAAATTTCTAAATAAATTACCTAGACTTTCTAAACATACTATTTT
AATGATTGTTTAGCTGTTTGTTTTGGGATATTTTGCAGATTTTACTGGGTAGTTTGGGCTAGTG
CTTATCCGCATTTTATATGGAATGATCAGCTTATGATAAGCACAAATGACGGATATGCATTTGCT
GAGGGCACAAGAGATATGATAGCTGGTTTTCATCAACCAAACGATCTTTCTTACTATGGCTCATC
TCTTTCGACGCTTAGCATGTGGTTATATAACATTTTGCCATTTTCATTAGAAACTATACTTTTGT
ATATGAGTACATTTTTATCTCCACTCTTAGCTGTGCCTTTGATACTTATAGGTAAAGAACTAAAC
GCTTCAAAAGCGGGTTTTATAGCTGCACTTCTAGCTATTATTGCAAATAGTTATTATAATAGAAC
AATGAGTGGATATTACGATACGGATATGCTAAATATCACTCTTCCTATGATGGTTTTTGGAGCA
TAACAAGACTTGTTCAAAGAAAAGAGAGAGTAAATTTAATATTTATTCCGGTTTTTATGGCGATA
TATGGATGGTGGTATCCATCTTCTTACTCACTATTACTTGCCATGATTGGAATGTTTTTTTATA
TACCATTGTTTTTGAAAGATACGAAAAACTAAACTATGAAGCTATGGTTTTATGATTTTAGCAA
TCACAAGCTTTTCTATACAAATTAAATTTATTATAGTTATTGTTTGTATGCTTTAATCTATTTT
TACCAAAGATTTTTTGATAAAAAAGTAATATTTGCATTAATTATGGCTTCGTTAATATGCTTTAT
ATGGCTTGGCGGGCTAAACCCTATACTTTTTAACATTAAATTTTATATATTTAGAGACATTGCAG
ATAGCGGTGATGCTGTTTTTAAATTTTTCAATGTAAATCAAACAATAAGAGAAAGTTCTGCGATA
GATTTAACACAGTTGTAACTAGGATTAGCGGGCATTTAATAGTATTTTGGTATCTATTATAGG
ATATATTTTATTTATAAAAAACAATAAAATTTTACTACTAACTTTACCGATTCTGTTTTGGGTC
TTATGTCATTTAAAAGTGGTTTAAGATTTACAATATACTCAGTTCCAGTAATGGCTCTTGGTTTT
GGCTATTTTGTTATGTATTGTTTTGCAAAAATAGATATAAAAGATCGTTTTTTAGGTTATGTGTT
TTTATTTGTTGTAACATTAGTGCATTATATCCATCTTTAAAACATATTTATGATTATAAAGTAT
TTCCTGTTTTTACACATAGCGAAGTTGAAAGTTTGGATAATTTAAAAAATATTGCAAAAGAGAA
GATTATGTGCTTTCTTGGTGGGATTATGGTTATCCGATCAGATATTATTCAGATGTAAAAACTCT
CATAGATGGAGGAAAACATCTTGGAAGTGATAACTTCGCCGTTAGCTTTGCACTTGGAAGCGATC
AAAATAGCTCTGCAAATATGGCAAGATTAGAAGTTGAATATACAGAAAAAAATTATGAAGAAAAA
TTTGGATTAAATTTAAAAAAGATGATGAAAGATTATAATGCTACAAATGTTAATGAGTTTTATT
ATCATTAAAAGATGAAAATTTAACTCTGCCAAAGCAAACAAGAGATATTTATTACTATTTACCAG
ATAGAATGATATACATATATCCGATAGTGCTAGATTTTCTAGACTTGATTGACAACAGGGCAA
GAATTTGCCCAGCCGTTTTTTATGGTTAGTGAGAGATTTTCAGCTACAAATGATAATCAAATAAT
GTTAAATAACAATGTCATATTAAGTAATGATGGCACTAAATTATCGATAAATGGCAACTCTTATA
GTGTAAATACATATGTTGAAACAAGTTATGATCAAACGAAAATTAAATGTAAATTATTTTAAC
ATAGATCCAAATAGCAATTTTATGTGATTTTATGAAGATTATTTGAGAATTTTGGTTTTAGA
TAAAACTTTGTATGATAGTGCGTATATTCAACTTTTTGTATTAGAAAATTATGATAAAAATTTAT
TTGAACCAGTGATTTTAAACGGATCAACTAAAATTTATAAACTCAAAAAATGA
```

FIG. 10 (SEQ ID NO: 23)

MSNFNFAKFLNKLPRLSKHTILMIVLAVCFGIFCRFYWVVWASAYPHFIWNDQLMISTNDGYAFA
EGTRDMIAGFHQPNDLSYYGSSLSTLSMWLYNILPFSLETILLYMSTFLSPLLAVPLILIGKELN
ASKAGFIAALLAIIANSYYNRTMSGYYDTDMLNITLPMMVFWSITRLVQRKERVNLIFIPVFMAI
YGWWYPSSYSLLLAMIGMFFLYTIVFERYEKLNYEAMVFMILAITSFSIQIKFIIVIVLYALIYF
YQRFFDKKVIFALIMASLICFIWLGGLNPILFNIKFYIFRDIADSGDAVFKFFNVNQTIRESSAI
DFNTVVTRISGHLIVFLVSIIGYILFIKNNKILLLTLPILFLGLMSFKSGLRFTIYSVPVMALGF
GYFVMYCFAKIDIKDRFLGYVFLFVVTFSALYPSLKHIYDYKVFPVFTHSEVESLDNLKNIAKRE
DYVLSWWDYGYPIRYYSDVKTLIDGGKHLGSDNFAVSFALGSDQNSSANMARLEVEYTEKNYEEK
FGLNLKKMMKDYNATNVNEFLLSLKDENLTLPKQTRDIYYYLPDRMIYIYPIVLDFSRLDLTTGQ
EFAQPFFMVSERFSATNDNQIMLNNNVILSNDGTKLSINGNSYSVNTYVETSYDQNEKLNVNYFN
IDPNSNFYVIFMKDYLRILVLDKTLYDSAYIQLFVLENYDKNLFEPVILNGSTKIYKLKK

GLYCOSYLATION METHOD

CROSS REFERENCE TO RELATED APPLICATIONS

This is a continuation of U.S. application Ser. No. 14/655,128, filed Jun. 24, 2015, which is the U.S. National Stage of International Application No. PCT/GB2014/050133, filed Jan. 17, 2014, which was published in English under PCT Article 21(2), which in turn claims the benefit of United Kingdom Application Nos. 1300956.8, filed Jan. 18, 2013, 1301023.6, filed Jan. 21, 2013, and 1309068.3, filed May 20, 2013.

FIELD OF THE INVENTION

The invention relates to microbial host cells engineered to produce glycoconjugate vaccines by stable integration of an oligosaccharyltransferase and optionally a carrier protein into the host's genome, wherein expression of the oligosaccharyltransferase is regulated.

BACKGROUND OF THE INVENTION

Bioavailability and bioactivity of small molecules, peptides, proteins or nucleic acids can be altered by glycosylation. Glycosylation is the transfer of an activated sugar moiety from a donor to an acceptor molecule and is catalysed by glycosyltransferases. Glycosylation of proteins occurs either co- or post-translationally by which a sugar moiety is attached to a nitrogen of asparagine or arginine side-chains forming N-linked glycans, or to the hydroxy oxygen of serine, threonine, tyrosine, lysine, or proline side-chains forming O-linked glycans, or less common forming C-linked glycans where the sugar is added to carbon on a tryptophan side-chain.

N-linked glycosylation is the most common post-translational modification and is carried out in the endoplasmic reticulum of eukaryotic cells. N-linked glycosylation can be of two main types; high mannose oligosaccharides which have two N-acetylglucosamines and complex oligosaccharides which include other types of sugar groups. The peptide motif contained in glycosylated polypeptides is Asn-X-Ser or Asn-X-Thr where X is any amino acid except proline. This is catalysed by the enzyme oligosaccharyltransferase [OT]; see Yan & Lennarz J. Bioi. Chem., Vol. 280 (5), 3121-3124 (2005). OT catalyses the transfer of an oligosaccharyl moiety (Glc3Man9GlcNAc2) from the dolichol-linked pyrophosphate donor to the side chain of an Asn. A pentasaccharide core is common to all N-linked oligosaccharides and serves as the foundation for a wide variety of N-linked oligosaccharides. O-linked glycosylation is less common. Serine or threonine residues are linked via their side chain oxygen to sugars by a glycosidic bond. Usually N-acetylglucosamine is attached in this way to intracellular proteins.

Most bacterial glycoproteins are associated with the bacterial cell surface or are secreted, suggesting a role for glycoproteins in the interaction with the host's immune system. Studies on the gram negative pathogenic bacterium *Campylobacter jejuni* identified a gene cluster involved in the synthesis of lipo-oligosaccharides and N-linked glycoproteins. The protein glycosylation locus, a cluster of 12 genes comprising pglA-pglG, is involved in the glycosylation of over 30 glycoproteins. Interestingly, these genes can be used to modify lipopolysaccharide structures in *Escherichia coli* providing a genetic tool to express heterologous recombinant glycoproteins. Studies performed with *C. jejuni* carrying mutations in the pglB and pglE genes showed impaired colonisation abilities in mice.

Polysaccharide antigens interact directly with B cells and induce antibody synthesis in the absence of T-cells. This T-cell independent immune response is limited as antibody production is low and is not normally boosted by re-immunisation. The antibody isotypes are dominated by IgM and IgG2, which are short lived and are generally of low affinity for a specific antigen. The ability to enhance the immunogenicity of polysaccharide antigens can be achieved by conjugation of the polysaccharide to a protein carrier. Glycoconjugate vaccines for *Streptococcus pneumoniae, Neisseria meningitidis* and *Haemophilus influenzae* are currently licensed for human use and are produced by linking the capsule (or other bacterial glycan-based structure such as lipooligosaccharide) from these bacteria to a protein toxoid. Whilst these vaccines provide a good level of immunity they are expensive and difficult to produce, requiring the purification of the glycan from the pathogenic organisms and chemical linkage to the carrier protein. The use of organic systems represents a more rapid and economical method for the production of glycoconjugates.

The production of glycoconjugates in an *E. coli* expression system requires the co-expression of three genes ["tri-plasmid"]: an acceptor protein, a polysaccharide biosynthetic locus and, for the coupling reaction, an oligosaccharyltransferase enzyme. Optimisation of co-expression in just one host is a lengthy process as it requires a tailored choice of the plasmids and optimised growth and expression conditions which are dependent on several factors. Additionally, the yield of glycoconjugates using such expression systems are often very low, which makes it commercial not viable.

The tri-plasmid system has a number of disadvantages. Compatible origins of plasmid replication need to be combined, a process that can take several months and restricts the choice of available plasmids. The use of three plasmids represents a considerable metabolic burden on the host bacterial strain and often the contents of one of the plasmids fail to express. Three different antibiotic selection markers for each of the plasmids need to be combined. This represents another burden on the host strain and clashes often result in sub-cloning of antibiotic resistance genes to find combinations that match. Additionally, some antibiotics resistance combinations are legally forbidden in some strains. Some glycosyltransferases [e.g. PgIB enzyme] responsible for linking the glycan to the protein has multiple transmembrane domains and is toxic to bacterial cells. Once expressed it has been found to reduce the growth of the host bacterial strain considerably. This significantly inhibits glycoconjugate yield. Heterologous expression of the polysaccharide coding genes and the resulting enzymes that are generated can result in high levels of toxicity to the host. Therefore, with some glycans it is impossible to find a tri-plasmid combination that allows for glycoconjugate production.

An example of the tri-plasmid system is disclosed in WO2009/104074 which describes the optimised production of conjugates comprising a protein carrier linked to an antigenic polysaccharide in an *E. coli* tri-plasmid expression system. The yield using this system is increased significantly by growing cells carrying three genes on two plasmids in a bioreactor under carefully monitored growth condition.

The present disclosure relates to a method providing the stable integration of genes into a bacterial genome for the production of glycoconjugates controlled by constitutive and regulated promoter elements which results in high yields of glycoconjugate. The application discloses also a method for the genetic manipulation of transposons facilitating easy and efficient preparation of the transposable element which allows integration of genes into the genome in one single step and additionally comprising also a tool which permits easy removal of the resistance marker once the gene of interest has integrated into the host genome.

Statements of the Invention

According to an aspect of the invention there is provided an isolated nucleic acid molecule comprising a transcription cassette adapted for expression in a bacterial host cell said cassette comprising: a nucleotide sequence encoding a glycosyltransferase enzyme wherein the expression of said enzyme is regulatable and a nucleotide sequence encoding an acceptor polypeptide for an oligosaccharide or monosaccharide wherein the acceptor polypeptide includes an amino acid sequence motif which is a substrate for the glycosyltransferase enzyme.

In a preferred embodiment of the invention the transcription cassette further comprises a regulatable promoter functionally linked to at least the nucleotide sequence encoding said glycosyltransferase enzyme.

In a preferred embodiment of the invention said promoter includes an inducible nucleotide element conferring regulatable expression in response to an inducer.

In a preferred embodiment of the invention said inducer is IPTG.

In an alternative embodiment of the invention said promoter includes a repressible nucleotide element conferring regulatable expression in response to a repressor.

In a preferred embodiment of the invention said repressor is the LacIq repressor.

Bacterial expression systems that utilize inducers and repressors of gene expression are well known in the art and include modifications that are well established which enhance induction or repression of gene expression. For example is lacIq carries a mutation in the promoter region of the lacI gene that results in increased transcription and higher levels of Lac repressor within the cells. Moreover, the Ptac, a strong hybrid promoter composed of the −35 region of the trp promoter and the −10 region of the lacUV5 promoter/operator and is strongly inducible.

In a preferred embodiment of the invention said glycosyltransferase is selected from the group consisting of: an oligosaccharyltransferase, a glucosyltransferase, a mannosyltransferase or a glucuronosyltransferase.

In a preferred embodiment of the invention said glycosyltransferase is an oligosaccharyltransferase, In a preferred embodiment of the invention said nucleic acid molecule encodes an oligosaccharyltransferase selected from the group consisting of:
  i) a nucleic acid molecule comprising a nucleotide sequence as set forth in SEQ ID NO 1 or SEQ ID NO: 22;
  ii) a nucleic acid molecule the complimentary strand of which hybridizes under stringent hybridization to SEQ ID NO: 1 or SEQ ID NO: 22 and encodes an oligosaccharyltransferase that recognizes the amino acid motif: D/E-X-N-X-S/T, wherein X is any amino acid except proline;
  iii) a nucleic acid molecule comprising a nucleotide sequence that is degenerate with respect to the nucleotide sequence in SEQ ID NO: 1 and which encodes a polypeptide comprising an amino acid sequence as represented in SEQ ID NO:2;
  iv) a nucleic acid molecule comprising a nucleotide sequence that is degenerate with respect to the nucleotide sequence in SEQ ID NO: 22 and which encodes a polypeptide comprising an amino acid sequence as represented in SEQ ID NO: 23;
  v) a variant sequence that varies from the amino acid sequences set forth in SEQ ID NO: 2 or 23 and which has oligosaccharyltransferase activity.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used.

Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology-Hybridization with Nucleic Acid Probes Part I, Chapter 2 (Elsevier, New York, 1993). The $T_m$ is the temperature at which 50% of a given strand of a nucleic acid molecule is hybridized to its complementary strand.

The following is an exemplary set of hybridization conditions and is not limiting.

Very High Stringency (Allows Sequences that Share at Least 90% Identity to Hybridize)
  i) Hybridization: 5×SSC at 65° C. for 16 hours
  ii) Wash twice: 2×SSC at room temperature (RT) for 15 minutes each
  iii) Wash twice: 0.5×SSC at 65° C. for 20 minutes each High Stringency (Allows Sequences that Share at Least 80% Identity to Hybridize)
  i) Hybridization: 5×-6×SSC at 65° C.-70° C. for 16-20 hours
  ii) Wash twice: 2×SSC at RT for 5-20 minutes each
  iii) Wash twice: 1×SSC at 55° C.-70° C. for 30 minutes each Low Stringency (Allows Sequences that Share at Least 50% Identity to Hybridize)
  i) Hybridization: 6×SSC at RT to 55° C. for 16-20 hours
  ii) Wash at least twice:2×-3×SSC at RT to 55° C. for 20-30 minutes each.

In a preferred embodiment of the invention said acceptor polypeptide includes the amino acid motif: Asn-X-Ser or Asn-X-Thr where X is any amino acid except proline.

In an alternative embodiment of the invention said acceptor polypeptide includes the amino acid motif: D/E-X-N-X-S/T, wherein X is any amino acid except proline.

In an alternative preferred embodiment of the invention said acceptor polypeptide including the amino acid motif D/E-X-N-X-S/T, wherein X is any amino acid except proline is selected from the group consisting of: DVNVT (SEQ ID NO: 24), EVNAT (SEQ ID NO: 25), DQNAT (SEQ ID NO: 26), DNNNT (SEQ ID NO: 27), DNNNS (SEQ ID NO: 28), DQNRT (SEQ ID NO: 29), ENNFT (SEQ ID NO: 30), DSNST (SEQ ID NO: 31), DQNIS (SEQ ID NO: 32), DQNVS (SEQ ID NO: 33), DNNVS (SEQ ID NO: 34), DYNVS (SEQ ID NO: 35), DFNVS (SEQ ID NO: 36), DFNAS (SEQ ID NO: 37), DFNSS (SEQ ID NO: 38), DVNAT (SEQ ID NO: 39), DFNVT (SEQ ID NO: 40) or DVNAS (SEQ ID NO: 41).

In a further preferred embodiment of the invention said transcription cassette comprises a nucleotide sequence that encodes one or more polysaccharide biosynthetic genes.

In a preferred embodiment of the invention said one or more biosynthetic genes are selected from the group consisting of the capsular polysaccharide or O antigen coding regions.

In a preferred embodiment of the invention said transcription cassette is adapted by the provision of one or more inverted repeat nucleotide sequences that are transposase recognition sequences.

In a preferred embodiment of the invention said recognition sequence comprises or consists essentially of the nucleotide sequences:

(SEQ ID NO:7) 5'-CTGTCTCTTGATCAGATCT-3' at the I end; and (SEQ ID NO: 8) 5'-ACTTGTGTATAAGAGTCAG-3', at the O end of the miniTn5 transposon.

In a preferred embodiment of the invention said transcription cassette further comprises a nucleotide sequence encoding a bacterial resistance marker gene.

In a preferred embodiment of the invention said bacterial resistance gene confers resistance to an antibiotic.

In a preferred of the invention said antibiotic is selected from the group consisting of: kanamycin, chloramphenicol, ampicillin, rifampicin, tetracycline, carbenecillin or Zeocin® [phleomycin: cas code 1006-33-0].

In a preferred embodiment of the invention said antibiotic is Zeocin®.

A skilled artisan is familiar with the use of different antibacterial markers. There are several classes of antibiotics targeting either the bacterial cell wall, cell membrane, interfere with essential bacterial enzymes, or target protein synthesis. Further, antibacterial antibiotics can target specific types of bacteria, such as Gram-negative or Gram-positive bacteria, whereas broad-spectrum antibiotics affect a wide range of bacteria.

In a preferred embodiment of the invention said bacterial resistance marker gene is adapted by the provision of 5' and 3' flanking nucleotide sequences that include recombination sites.

In a preferred embodiment of the invention said recombination sites comprise or consist essentially of the nucleotide sequence:

5' end loxP sequence: (SEQ ID NO: 9) 5'-ATAACTTCG-TATAATGTAT GCTATACGAA GTAG-3'.

3' end loxP sequence: (SEQ ID NO:10) 5'-ATAAC TTCG-TATAATGTATGCTATA CGAAGTTAT-3' for the CRE LOX system or (SEQ ID NO: 11) 5'-GAAGT TCCTATTCCG AAGTTC-CTAT TCTCTAGAAAGTATAGGAAC TTC-3' and (SEQ ID NO:12) 5'-GAAGTACCTATTC CGAAGT-TCCT ATTCTCTAGA AAGTATAGGA ACTTC-3' for the FRT FLP system.

According to a further aspect of the invention there is provided a vector comprising a transcription cassette according to the invention.

In a preferred embodiment of the invention said vector is a plasmid.

In an alternative preferred embodiment of the invention said vector is a transposon.

In a preferred embodiment of the invention said transposon is selected from the group consisting of: Tn5, Tn10, Himar1 and other mariner elements, Tn7, Tn917, Tn916.

In a preferred embodiment of the invention said transposon is Tn5.

According to a further aspect of the invention there is provided a bacterial cell genetically modified with a transcription cassette or vector according to the invention.

In a preferred embodiment of the invention said bacterial cell is a pathogenic Gram-positive bacterial cell.

In a preferred embodiment of the invention said bacterial cell is a pathogenic Gram-negative bacterial cell.

In a preferred embodiment of the invention said bacterial cell is a human pathogen.

In a preferred embodiment of the invention said human pathogen is selected from the group: *Neisseria, Moraxella, Escherichia, Salmonella, Shigella, Pseudomonas, Helicobacter, Legionella, Haemophilus, Klebsiella, Enterobacter, Cronobacter* and *Serratia*.

In a preferred embodiment of the invention said bacterial cell is a non-human pathogen.

In a preferred embodiment of the invention said non-human pathogen is selected from group: *Mannheimia* spp., *Actinobacillus* spp. e.g *Actinobacillus pleuropneumoniae, Pasteurella* spp., *Haemophilus* spp. or *Edwardsiella* spp.

In a preferred embodiment of the invention said bacterial cell is a zoonotic bacterial species.

In a preferred embodiment of the invention said zoonotic bacterial species is selected from the group: *Brucella* spp., *Campylobacter* spp., *Vibrio* spp., *Yersina* spp. and *Salmonella* spp.

According to a further aspect of the invention there is providing a bacterial cell culture comprising a genetically modified bacterial cell according to the invention.

According to an aspect of the invention there is provided a transcription cassette or vector according to the invention for use in the production of one or more glycoconjugates.

According to a further aspect of the invention there is provided a process for the production of one or more glycoconjugates comprising:

i) providing a bacterial cell culture according to the invention;

ii) providing cell culture conditions; and iii) isolating one or more glycoconjugates from the bacterial cell or cell culture medium.

According to a further aspect of the invention there is provided a cell culture vessel comprising a bacterial cell culture according to the invention.

In a preferred embodiment of the invention said cell culture vessel is a fermentor.

Bacterial cultures used in the process according to the invention are grown or cultured in the manner with which the skilled worker is familiar, depending on the host organism. As a rule, bacteria are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The products produced can be isolated from the bacteria as described above by processes known to the skilled worker, for example by extraction, distillation, crystallization, if appropriate precipitation with salt, and/or chromatography. In this process, the pH value is advantageously kept between pH 4 and 12, preferably between pH 6 and 9, especially preferably between pH 7 and 8.

An overview of known cultivation methods can be found in the textbookBioprocess technology 1. Introduction to Bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Brunswick/Wiesbaden, 1994)).

The culture medium to be used must suitably meet the requirements of the bacterial strains in question. Descriptions of culture media for various bacteria can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogenphosphate or dipotassiumhydrogenphosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing bacteria usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case.

Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

According to a further aspect of the invention there is provided a method for the stable integration of a transposable element into a bacterial genome comprising:
  i) forming a cell culture preparation comprising a bacterial cell and a transposon according to the invention;
  ii) incubating the preparation to allow stable integration of the transposon;
  iii) selecting bacterial cells that have stably integrated the transposon using culture conditions that select for bacterial cells that are stable integrants; and
  iv) cloning bacterial cells that have stably integrated the transposon.

In a preferred method of the invention said selection is an antibiotic selection using a bacterial resistance marker gene.

In a preferred method of the invention the cloned bacterial cells are contacted with a vector comprising a nucleotide sequence that encodes a recombinase that deletes all or part of said bacterial resistance marker gene.

In a preferred embodiment of the invention said recombinase is specific for recombination sites comprising or consisting essentially of the nucleotide sequence set forth in SEQ ID NO: 13 or 14.

According to a further aspect of the invention there is provided a process for the identification of novel glycoconjugates comprising:
i) forming a cell culture preparation comprising a bacterial cell and a transposon according to the invention;
ii) incubating the preparation to allow stable integration of the transposon;
iii) selecting bacterial cells that have stably integrated the transposon using culture conditions that select for bacterial cells that are stable integrants;
iv) cloning bacterial cells that have stably integrated the transposon;
v) isolating glycoconjugates from the cloned bacterial cells or cell culture medium; and
vi) analysing the monosaccharide or polysaccharide content of said isolated glycoconjugate.

According to a further aspect of the invention there is provided a glycoconjugate formed by the process according to the invention.

According to a further aspect of the invention there is provided a method for the delivery of a transposable element to a bacterial cell comprising:
i) providing a vector adapted for high copy number replication in a bacterial cell comprising: a nucleotide sequence of an expression cassette according to the invention, a nucleotide sequence encoding an antibiotic resistance gene cassette wherein the antibiotic resistance gene cassette is flanked by recombination sequences recognized by a recombinase and wherein the cassettes are flanked by restriction sites for excision and delivery into a transposon delivery vector;
ii) providing a transposon delivery vector comprising restriction sites flanked by inverted repeats for delivery of a transposable element to a bacterial cell;
iii) sub-cloning the vector in (i) into the delivery vector in (ii) to provide a modified delivery vector;
iv) transferring the modified delivery vector in (iii) to a bacterial cell and selecting stably integrated bacterial cells by antibiotic resistance;
v) cloning stably integrated bacterial cells; and optionally
vi) transforming the stably integrated bacterial cells with a vector comprising a nucleotide sequence encoding a recombinase that excises the antibiotic resistance genes from the genome of the stably integrated bacterial cells.

Delivery vectors for the transposable elements such as TN5 transposons are known in the art and have significant limitations. For example, the pUT delivery vector includes a R6K origin of replication which limits transformation to *E. coli* strains that are Apir positive. The development of a high copy number intermediate vector considerably expands the type of bacterial host cell and significantly simplifies the modification of bacterial cells using transposable element.

According to a further aspect of the invention there is provided a kit comprising: a vector adapted for high copy number replication in a bacterial cell wherein the vector comprises: a nucleotide sequence encoding an antibiotic resistance gene cassette and a multiple cloning site for the insertion of an expression cassette according to the invention wherein the antibiotic gene cassette is flanked by recombination sequences recognized by a recombinase and wherein the multiple cloning sites are flanked by restriction sites enabling the excision of the expression cassette.

In a preferred embodiment of the invention said kit further comprises a transposon delivery vector comprising restriction sites flanked with transposase recognition nucleotide sequences.

In a further preferred embodiment of the invention said kit further comprises a recombinase, for example a flippase.

In a preferred embodiment of the invention the kit further includes a bacterial strain or strains compatible with the transposon.

In a preferred embodiment of the invention said kit optionally includes a nucleic acid molecule encoding a glycosyltransferase and a nucleic acid molecule that encodes one or more polysaccharide biosynthetic genes.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures;

BRIEF DESCRIPTION OF THE DRAWINGS

FIG. 3A PglB nucleotide sequence (SEQ ID NO: 1);

FIG. 3B the full length PglB amino acid sequence (SEQ ID NO: 2);

FIG. 4 is the nucleotide sequence encoding for the CRE LOX system recombinase (SEQ ID 13);

FIG. 5 is the nucleotide sequence encoding the FLP FRT recombinase (SEQ ID 14);

FIG. 6 Glycosylation of AcrA with *S. pneumoniae* capsular polysaccharide. Anti-HIS western blot. Lane 1, AcrA only control; 2 *E. coli* W3110 carrying AcrA and PglB on the chromosome due to an insertion of pEFNOV19: Coding for an IPTG inducible copy of CjPglB and constitutively expressed AcrA from a Tetracycline resistance cassette promoter on a pUTminiTn5km2 backbone. Arrows indicate shift in the size of AcrA only when all the glycosylating components are together.

FIG. 9 is the nucleotide sequence of *Campylobacter sputorum* PglB (SEQ ID NO: 22); and FIG. 10 *Campylobacter sputorum* protein sequence of PglB (SEQ ID NO: 23).

Materials and Methods

Construction of pJAN25

Figure 1:
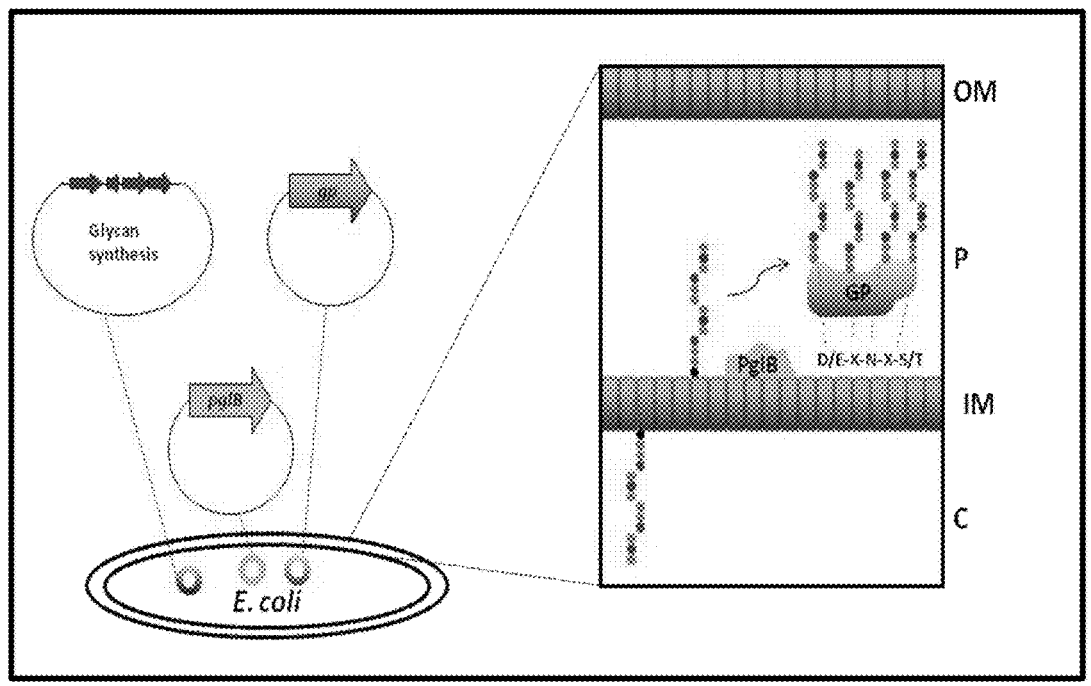
FIG. 1: The tri-plasmid system currently used to generate a glycoconjugate vaccine in *E. coli*. C, cytoplasm; IM, inner membrane; P, periplasm; OM, Outer Membrane.
Figure 2:
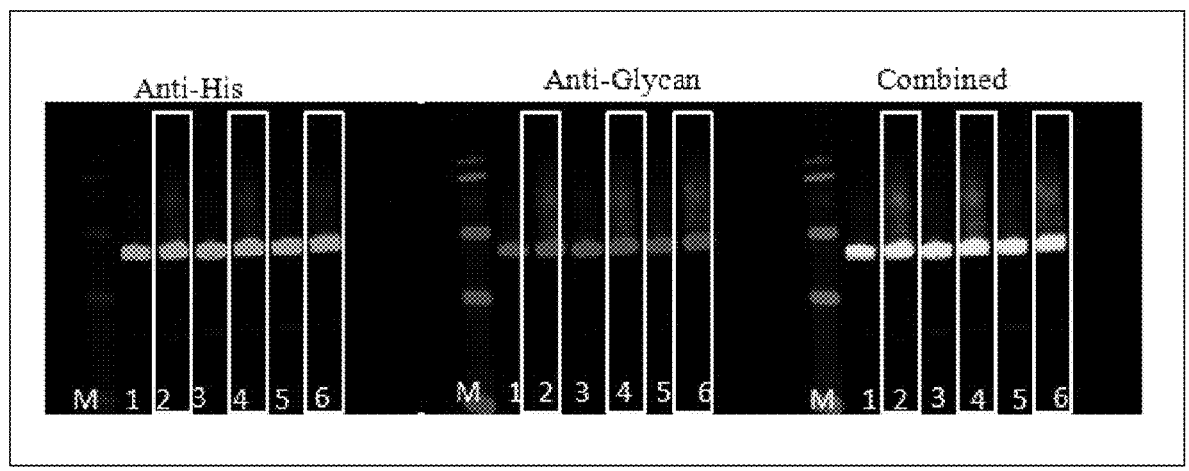
FIG. 2: Chromosomal insertion CjPglB generates superior glycoconjugate yield compared to the standard three plasmid system; AcrA purified from *E. coli* CLM24 carrying chromosomal PglB tested by western blot (lanes 2/4/6) compared to plasmid borne PglB (lanes 1/3/5)

The gene coding for *C. jejuni* PglB was amplified by PCR with the pTac promoter and LacI repressor from plasmid pEXT20 as a template using Pfx Polymerase with (SEQ ID 15: 5'-TTTTGCGGCCGCTTCTACGTGTTCCGCTTCC-3') as forward primer and (SEQ ID 16: 5'-TTTTGCGGC-CGCATTGCGTTGCGCTCACTGC-3') reverse primer using the following cycling conditions, 94° C./2 minutes followed by 35 cycles of 94° C. for 30 seconds, 56° C. for 30 seconds and 68° C. for 4 minutes. The PCR product was then cloned in pJET2.0 plasmid (Thermo Scientific U.K.) according to the manufacturer's instructions and named pOST9. The plasmid was maintained in into *E. coli* DH5a (Stratagene U.K.) The vector pOST9 cut with the restriction enzyme NotI (New England Biolabs U.K. Ltd.) and ligated into the unique NotI site in pUTminiTn5km2 resulting in plasmid pJAN25 and maintained in Transformax *E. coli* strain EC100D pir+ (Cambio U.K.).

Construction of pFEB11

The gene coding for *C. jejuni* AcrA was amplified by PCR with the ter cassette promoter and chloramphenicol resistance cassette from the plasmid pMH5 as a template using (SEQ ID 17: 5'-TTTTGCGGCCGCTTCTCATGTTT-GACAGCTTATC-3') as forward primer and (SEQ ID 18: 5'-TTTTGCGGCCGCAGCGAGTCAGTGAGCGAGG-3') reverse primer using the following cycling conditions, 94° C./2 minutes followed by 35 cycles of 94° C. for 30 seconds, 56° C. for 30 seconds and 68° C. for 2 minutes. The product was cut by NotI and cloned into the unique NotI site in pUTminiTn5km2 resulting in plasmid pFEB11 and maintained in Transformax *E. coli* strain EC100D pir+ (Cambio U.K.).

Construction of pEFNOV19

The gene coding for *C. jejuni* AcrA was amplified by PCR with the tet cassette promoter and cam resistance cassette from the plasmid pMH5 as a template using (SEQ ID 19: 5'-TTTTGCGATCGCTTCTCATGTTTGACAGCTTATC-3') as forward primer and (SEQ ID 20: 5'-TTTTAGGC-CTAGCGAGTCAGTGAGCGAGG-3') as reverse primer 94° C./2 minutes followed by 35 cycles of 94° C. for 30 seconds, 56° C. for 30 seconds and 68° C. for 2 minutes. The product was cut by AsisI and StuI (New England Biolabs U.K. Ltd) and cloned in AsisI and StuI digested pJAN25 generating the plasmid pEFNOV19 and maintained in Transformax *E. coli* strain EC100D pir+ (Cambio U.K.).

Construction of pJCUSA1

We devised a novel transposon cargo loading procedure where the cloning experiments are carried out within a modified version of the commercially available high copy number vector pUC57, this modified plasmid has a chloramphenicol resistance cassette in its backbone from plasmid pMH5 and a Zeocin® resistance cassette flanked by loxP sites allowing for downstream removal of antibiotic marker from the final target strain via the introduction of the CRE enzyme. It has a pMB1 origin of replication and thus can be maintained in any *E. coli* strain prior to being cut out and transferred along with the Zeocin® resistance cassette using SfiI restriction enzyme digestion and transfer into the pUT delivery vector thus generating a functional transposon. The sequence of this novel construct is shown below (SEQ ID 21):

5'GGCCGCCTAGGCCGCGGCCGCCTACTTCGTATAGCATACATTATACGA

AGTTATGTCTGACGCTCAGTGGAACGACGCGTAACTCACGTTAAGGGATT

TTGGTCATGATCAGCACGTTGACAATTAATCATCGGCATAGTATATCGGC

ATAGTATAATACGACAAGGTGAGGAACTAAAACATGGCCAAGTTGACCAG

TGCCGTTCCGGTGCTCACCGCGCGCGACGTCGCCGGAGCGGTCGAGTTCT

GGACCGACCGGCTCGGGTTCTCCCGGGACTTCGTGGAGGACGACTTCGCC

GGTGTGGTCCGGGACGACGTGACCCTGTTCATCAGCGCGGTCCAGGACCA

GGTGGTGCCGGACAACACCCTGGCCTGGGTGTGGGTGCGCGGCCTGGA

CGAGCTGTACGCCGAGTGGTCGGAGGTCGTGTCCACGAACTTCCGGGAC

GCCTCCGGGCCGGCCATGACCGAGATCGGCGAGCAGCCGTGGGGGCGG

GAGTTCGCCCTGCGCGACCCGGCCGGCAACTGCGTGCACTTCGTGGCCG

AGGAGCAGGACTGAATAACTTCGTATAGCATACATTATACGAAGTTATGG

CCGCCTAGGCC-3'.

Bacterial Conjugation

To enable transfer of the pglB and acrA transposon cargo into the chromosome of a recipient *E. coli* strain the plasmids pJAN25, pFEB11 or pEFNOV19 were transferred into the *E. coli* strain19851 pir⁺ for direct mating. When necessary the donor *E. coli* strain used was *E. coli* MFD a diaminopimelic acid (DAP) auxotroph. Growth medium was supplemented with kanamycin 50 µg/ml and ampicillin 100 µg/ml for pJAN25 or pFEB11 whilst chloramphenicol 30 µg/ml and ampicillin 100 µg/ml were added to maintain pEFNOV19. Both donor and recipient bacteria were growth until late exponential phase. Bacterial cells were pelleted by centrifugation, washed 3 times with PBS and mixed together in a ratio of 1:3 recipient to donor and spotted on a dry LB agar plate with no antibiotics for 4-8 hrs. The cells were scraped and suspended in PBS and dilutions plated on LB agar with appropriate selection antibiotics to select for transconjugants. Individual colonies were picked up and screened for loss of the pUT backbone and for the presence of the transposon.

Generation of Unmarked pglB Insertion

The transposon carrying pglB and loxP recombination sites around a Zeocin® resistance cassette was introduced into *E. coli*. Following selection for Zeocin® resistant colonies, the antibiotic selection marker was removed by introduction via electroporation, the temperature sensitive vector pCRE5 (Reference: Appl Environ Microbiol. 2008 February; 74(4): 1064-1075. Genetic Tools for Select-Agent-Compliant Manipulation of Burkholderia pseudomallei. Kyoung-Hee Choi, Takehiko Mima, Yveth Casart, Drew Rholl, Ayush Kumar, Ifor R. Beacham and Herbert P. Schweizer).

*E. coli* was cultured at 28° C. in the presence of kanamycin 50 µg/ml, rhamnose was added to induce expression at 0.2% final concentration and the organism subcultured several times to select for colonies that had lost resistance to Zeocin® but maintained resistance to kanmaycin indicating that the bleomycin resistance gene had been flipped out of the chromosome.

This *E. coli* mutant was then sub-cultured at 42° C. to cure out the pCRE5 plasmid. Screening for colonies that had once again become sensitive to kanamycin confirmed loss of pCRE5 and completed generation of an unmarked inducible copy of pglB on the chromosome of *E. coli*.

To test glycosylation, this *E. coli* strain was transformed with the plasmid pACYCpglB::kan (Linton Molecular Microbiology (2005) 55(6), 1695-1703 Functional analysis of the *Campylobacter jejuni* N-linked protein glycosylation pathway. Dennis Linton, Nick Dorrell, Paul G. Hitchen, Saba Amber, Andrey V. Karlyshev, Howard R. Morris, Anne Dell, Miguel A. Valvano, Markus Aebi and Brendan W. Wren) and the plasmid pWA2 coding for the HIS tagged acceptor protein AcrA (PNAS vol. 102, pp 3016-3021. Engineering N-linked protein glycosylation with diverse O antigen lipopolysaccharide structures in *Escherichia coli*. Mario F. Feldman, Michael Wacker, Marcela Hernandez, Paul G. Hitchen, Cristina L. Marolda, Michael Kowarik, Howard R. Morris, Anne Dell, Miguel A. Valvano, and Markus Aebi).

10 ml of LB broth carrying 30 µg/ml of chloramphenicol and 100 µg/ml of ampicillin to select for pACYCpglB::kan were inoculated with a single colony of *E. coli* strain W3110pglB.

Cultures were incubated at 37° C. with shaking until an optical density 600 nm of 0.6 was reached. IPTG was added to a final concentration of 1 mM and the cultures were incubated for a further 16 hours overnight. Protein was HIS purified and western blots carried out using anti campy glycan and anti HIS antibodies and the images visualised on an Odyssey LI-COR® scanner.

EXAMPLE 1

The *E. coli* strain W3110 carrying a plasmid coding for a *Streptococcus pneumonia* capsular polysaccharide encoded on the plasmid pB4-4 was subjected to conjugation with *E. coli* 19851 pir+ carrying the plasmid pFEB19 coding for an IPTG inducible copy of pglB and a constitutively expressed copy acrA. Previous attempts to make a glycoconjugate using the standard three plasmid system failed presumably due to the combined toxicity of PglB and the metabolic burden of the polysaccharide coding region. The transposon system resulted for the first time in a stable strain. IPTG was added to induce chromosomal expression of pglB and HIS tagged AcrA was purified from the cells using NiNTA binding. FIG. 6 demonstrates how AcrA is shifted in size due to the addition of glycan to the acceptor protein (lane 2). This shift in size does not occur when the glycan is not present (lane 1).

EXAMPLE 2

We have used the transposon pJAN25 carrying an IPTG inducible copy of CjpglB to integrate this gene into the chromosomes of glycoengineering *E. coli* strains W3110, CLM24, CLM37, Se874, SCM7, SCM6, SCM3.

EXAMPLE 3

We have used the transposon pJAN25 carrying an IPTG inducible copy of CjpglB to integrate this gene into the chromosomes of the following organisms: *Vibrio cholerae, Yersinia pseudotuberculosis, Citrobacter freundii, Actinobacillus pleuropneumoniae*. In the case of *Vibro cholerae* and *Actinobacillus pleuropneumoniae* the standard glycoengineering plasmids used in the tri-plasmid system could not be normally maintained in these organisms.

Figure 7:
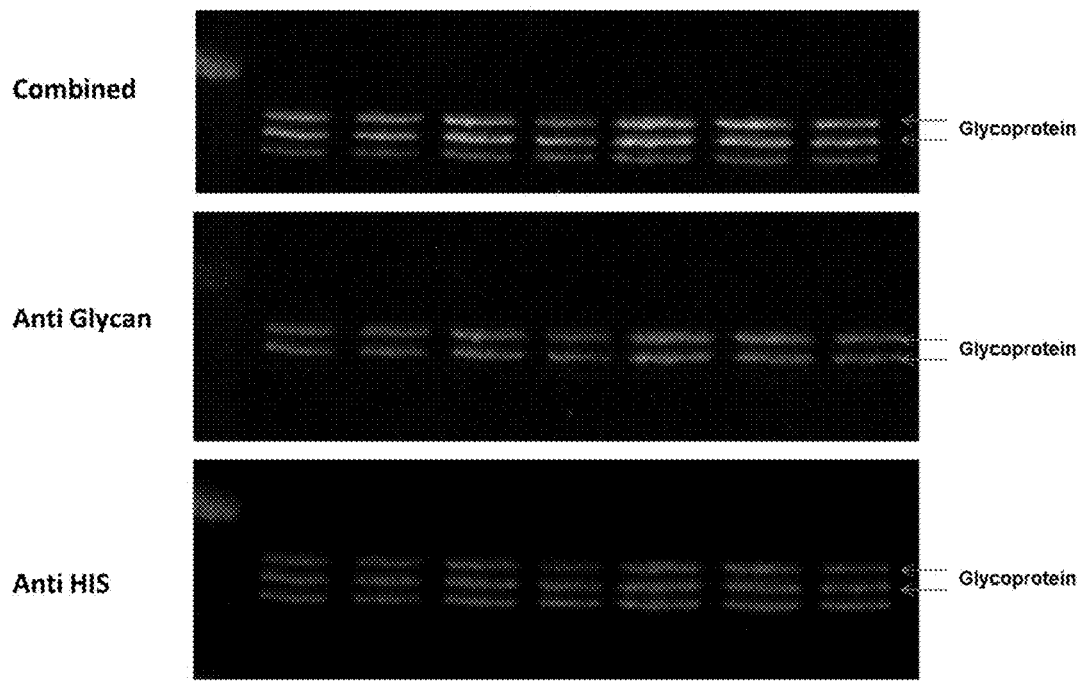
FIG. 7 Demonstration of acceptor protein glycosylation. Western blot using anti-glycan (B), anti-His (C) and both antibodies combined (A). AcrA glycosylated with *C. jejuni* heptasaccharide within *E. coli* W3110 cells carrying unmarked pglB insertion.

EXAMPLE 4 pJCUSA1 has been used to generate a transposon with an IPTG inducible copy of CjpglB and a Zeocin® resistance cassette flanked by loxP recombination sites. This was delivered into a recipient *E. coli* strain by conjugation. This strain can be cured of Zeocin® resistance by the introduction of a CRE recombinase coding plasmid that has a temperature sensitive origin of replication leading to an unmarked *E. coli* strain capable of generating a glycoconjugate. This is illustrated in FIG. 7. The method is used to generate an unmarked chromosomal insertion of the oligosaccharyltransferase coding gene pglB which is exemplified by glycosylation of an acceptor protein.

EXAMPLE 5

Demonstration of the integration of *Campylobacter jejuni* PglB into the chromosome of *Actinobacillus pleuropneumoniae* serotype 8.

*E. coli* Mu free donor cells (MFD) were transformed with the plasmid pJAN25: Coding for an IPTG inducible copy of CjPglB carried on a pUTminiTn5km2 transposon backbone. This donor strain was conjugated with *Actinobacillus pleuropneumoniae* serotype 8 and colonies screened for gain of resistance to kanamycin and no resistance to ampicillin indicating that the transposon had left thebackbone and inserted into the chromosome of *A. pleuropneumoniae*.

To demonstrate that this chromosomally inserted copy of pglB was active, membranes were isolated from the newly constructed mutant of *A. pleuropneumoniae* after expression of pglB was induced. 16 h *A. pleuropneumoniae* cultures were diluted 1:25 in fresh media and grown to an OD600 of 0.4-0.6. Expression was induced at this point by addition of IPTG to 1 mM. Incubation was resumed for a further 16 h. Cells were harvested by centrifugation.

Solubilized membranes were prepared by isolating cells expressing CjPglB and by re-suspending the bacterial cell pellet in 2 ml 50 mM Tris-HCl (pH 7.0), 25 mM NaCl and then lysing the pellet using a GE50 ultrasonic processor. Lysates were centrifuged twice at 40 000×g, 4° C. for 20 min to remove unbroken cells. The supernatant was ultracentrifuged at 100 000×g, 4° C. for 1 h, and the resulting total membrane pellet resuspended in 2 ml 50 mM Tris-HCl (pH 7.0), 25 mM NaCl, 1% Triton X-100 per gram of initial wet cell pellet. Samples were incubated at room temperature for 1 h then ultracentrifuged once more at 100 000×g, 4° C. for 1 hour. Supernatants were collected as Triton X-100-solubilised membrane fractions.

Figure 8:
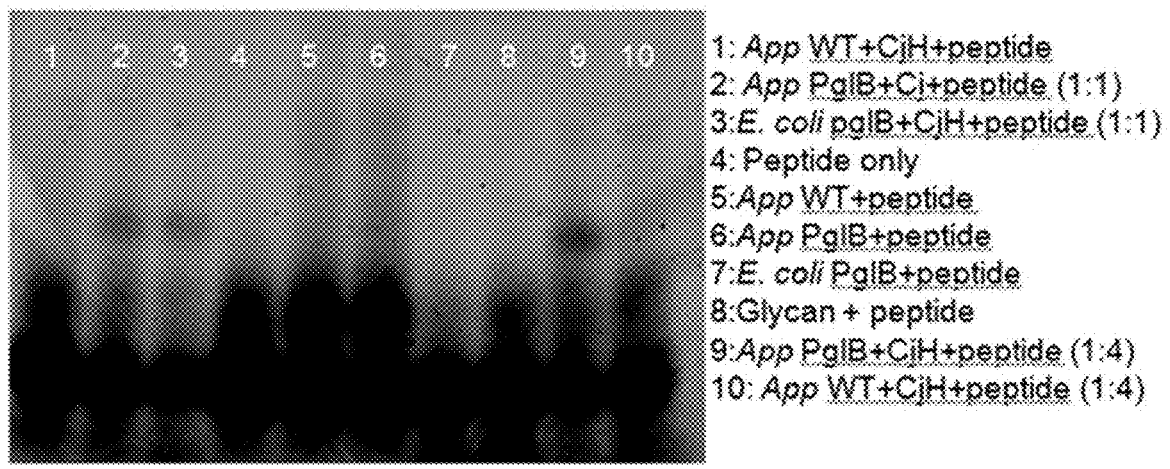
FIG. 8 In vitro glycosylation of peptide using pglB expressed in *A. pleuropneumoniae* (App). Reduced mobility of peptide is seen only in test lanes 2 and 9 where membranes from *A. pleuropneumoniae* coding for PglB are used. Lane 3 is a positive control reaction carrying *E. coli* membranes expressing PglB and Lanes 1, 4, 5, 6, 7, 8 and 10 are negative controls demonstrating that peptide shift only occurs when pglB is expressed in *A. pleuropneumoniae* or *E. coli* and combined with the correct glycan.

The in vitro assay was performed by preparing reaction mixtures that typically contained 3 µl of the fluorescently-labelled peptide FAM-ADQNATA-NH2 (30 µM), 1 µl MnCl2 (150 mM), 4 µl membranes from *A. pleuropneumoniae* expressing CjPglB and 22 µl membrane preparation from *E. coli* expressing the *C. jejuni* heptasaccharide. Samples were incubated at 30° C. with agitation for 16 h. Reactions were stopped by the addition of 10 µl 4×SDS-PAGE gel loading buffer and incubated at 95° C. for 5 min. Samples were loaded on a 4-16% Tricine gel and separated by SDS-PAGE at 30 V for 30 min followed by 200 V for 60 min. Fluorescent peptides were visualized using a Typhoon Trio Imager (FIG. 8).

The invention claimed is:

1. A genetically modified bacterial cell, comprising:
   i) a transcription cassette comprising the nucleic acid molecule of SEQ ID NO: 22; or
   ii) transcription cassette comprising a nucleic acid molecule with a nucleic acid sequence that is degenerate with respect to the nucleotide sequence of SEQ ID NO: 22 and encodes an oligosaccharyltransferase enzyme comprising the amino acid sequence of SEQ ID NO: 23;

and a nucleic acid molecule encoding one or more heterologous polysaccharide biosynthetic genes.

2. The genetically modified bacterial cell of claim 1, wherein said cell is further transformed with a nucleic acid molecule encoding an acceptor polypeptide for an oligosaccharide or monosaccharide, wherein the acceptor polypeptide includes an amino acid motif which is a substrate for the oligosaccharyltransferase enzyme.

3. The genetically modified bacterial cell of claim 1, wherein the transcription cassette comprises a regulatable promoter functionally linked to the nucleic acid molecule of SEQ ID NO: 22 or to the nucleic acid sequence that is degenerate with respect to the nucleotide sequence of SEQ ID NO: 22 encoding said oligosaccharyltransferase enzyme.

4. The genetically modified bacterial cell of claim 3, wherein said regulatable promoter comprises an inducible nucleotide element conferring regulatable expression in response to an inducer.

5. The genetically modified bacterial cell of claim 3, wherein said regulatable promoter comprises a repressible nucleotide element conferring regulatable expression in response to a repressor.

6. The genetically modified bacterial cell of claim 1, wherein the transcription cassette comprises a constitutive promoter conferring constitutive expression of the nucleic acid molecule of SEQ ID NO: 22 or the nucleic acid sequence that is degenerate with respect to the nucleotide sequence of SEQ ID NO: 22 encoding said oligosaccharyltransferase enzyme.

7. The genetically modified bacterial cell of claim 2, wherein said acceptor polypeptide comprises the amino acid motif Asn-X-Ser or Asn-X-Thr, wherein X is any amino acid except proline.

8. The genetically modified bacterial cell of claim 7, wherein said acceptor polypeptide comprises the amino acid motif: D/E-X—N-X-S/T, wherein X is any amino acid except proline.

9. The genetically modified bacterial cell of claim 1, wherein said one or more heterologous polysaccharide biosynthetic genes encode capsular polysaccharides or O antigens.

10. The genetically modified bacterial cell of claim 1, wherein said bacterial cell is a human pathogen.

11. The genetically modified bacterial cell of claim 2, wherein said bacterial cell is a human pathogen.

12. The genetically modified bacterial cell of claim 10, wherein said human pathogen is an *Neisseria, Moraxella, Escherichia, Salmonella, Shigella, Pseudomonas, Helicobacter, Legionella, Haemophilus, Klebsiella, Enterobacter, Cronobacter* or *Serratia*.

13. The genetically modified bacterial cell of claim 11, wherein said human pathogen is an *Neisseria, Moraxella, Escherichia, Salmonella, Shigella, Pseudomonas, Helicobacter, Legionella, Haemophilus, Klebsiella, Enterobacter, Cronobacter* or *Serratia*.

14. The genetically modified bacterial cell of claim 1, wherein said bacterial cell is a non-human pathogen.

15. The genetically modified bacterial cell of claim 2, wherein said bacterial cell is a non-human pathogen.

16. The genetically modified bacterial cell of claim 14, wherein said non-human pathogen is a *Mannheimia* spp., *Actinobacillus* spp., *Pasteurella* spp., *Haemophilus* spp. or *Edwardsiella* spp.

17. The genetically modified bacterial cell of claim 15, wherein said non-human pathogen is an *Mannheimia* spp., *Actinobacillus* spp., *Pasteurella* spp., *Haemophilus* spp. or *Edwardsiella* spp.

18. The genetically modified bacterial cell of claim 1, wherein said bacterial cell is a zoonotic bacterial species.

19. The genetically modified bacterial cell of claim 18, wherein said zoonotic bacterial species is a *Brucella* spp., *Campylobacter* spp., *Vibrio* spp., *Yersina* spp. or *Salmonella* spp.

20. A process for producing one or more glycoconjugates, comprising:
   i) culturing the genetically modified bacterial cell of claim 1 in a cell culture medium; and
   ii) isolating one or more glycoconjugates from the genetically modified bacterial cell or cell culture medium.

21. A process for producing one or more glycoconjugates, comprising:
   i) culturing the genetically modified bacterial cell of claim 2 in a cell culture medium; and
   ii) isolating one or more glycoconjugates from the genetically modified bacterial cell or cell culture medium.

22. A transposon, comprising:
   a transcription cassette adapted for expression in a bacterial host cell, wherein the transcription cassette comprises:
   i) a nucleic acid molecule comprising the nucleotide sequence of SEQ ID NO: 22; or
   ii) a nucleic acid molecule with a sequence that is degenerate with respect to the nucleotide sequence of SEQ ID NO: 22 and encodes an oligosaccharyltransferase enzyme comprising the amino acid sequence of SEQ ID NO: 23;

and a nucleic acid molecule encoding a bacterial resistance marker gene.

23. An isolated nucleic acid molecule, comprising
   a transcription cassette adapted for expression in a bacterial host cell, wherein the transcription cassette comprises:
   i) a nucleic acid molecule comprising the nucleotide sequence of SEQ ID NO: 22; or ii) a nucleic acid molecule with a sequence that is degenerate with respect to the nucleotide sequence of SEQ ID NO: 22 and encodes an oligosaccharyltransferase enzyme comprising the amino acid sequence of SEQ ID NO:23, and a heterologous promoter operably linked to the nucleic acid molecule of i) or ii).

24. The isolated nucleic acid molecule of claim 23, wherein said transcription cassette further comprises a nucleic acid molecule encoding a bacterial resistance marker gene.

25. The isolated nucleic acid molecule of claim 24, wherein said bacterial resistance gene confers resistance to an antibiotic.

26. The genetically modified bacterial cell of claim 16, wherein said non-human pathogen is an *Actinobacillus pleuropneumoniae*.

27. The genetically modified bacterial cell of claim 17, wherein said non-human pathogen is an *Actinobacillus pleuropneumoniae*.

* * * * *

SEQUENCE LISTING

<160> NUMBER OF SEQ ID NOS: 41

<210> SEQ ID NO 1
<211> LENGTH: 2142
<212> TYPE: DNA
<213> ORGANISM: Campylobacter jejuni

<400> SEQUENCE: 1

| | | | | | |
|---|---|---|---|---|---|
| atgttgaaaa | aagagtattt | aaaaaaccct | tatttagttt | tgtttgcgat | gattatatta | 60 |
| gcttatgttt | ttagtgtatt | ttgcaggttt | tattgggttt | ggtgggcaag | tgagtttaat | 120 |
| gagtattttt | tcaataatca | gttaatgatc | atttcaaatg | atggctatgc | ttttgctgag | 180 |
| ggcgcaagag | atatgatagc | aggttttcat | cagcctaatg | atttgagtta | ttatggatct | 240 |
| tctttatccg | cgcttactta | ttggctttat | aaaatcacac | cttttctctt | tgaaagtatc | 300 |
| attttatata | tgagtacttt | tttatcttct | ttggtggtga | ttcctactat | tttgctagct | 360 |
| aacgaataca | aacgtccttt | aatgggcttt | gtagctgctc | ttttagcaag | tatagcaaac | 420 |
| agttattata | atcgcactat | gagtgggtat | tatgatacgg | atatgctggt | aattgttttg | 480 |
| cctatgtttt | ttttattttt | tatggtaaga | atgattttaa | aaaagacttt | tttttcattg | 540 |
| attgccttgc | cgttatttat | aggaatttat | ctttggtggt | atccttcaag | ttatacttta | 600 |
| aatgtagctt | taattggact | ttttttaatt | tatacactta | tttttcatag | aaaagaaaag | 660 |
| attttttata | tagctgtgat | tttgtcttct | cttactcttt | caaatatagc | atggttttat | 720 |
| caaagtgcca | ttagtaat | acttttgct | ttattcgcct | tagagcaaaa | acgcttaaat | 780 |
| tttatgatta | taggaattt | aggtagtgca | actttgatat | ttttgatttt | aagtggtggg | 840 |
| gttgatccta | tactttatca | gcttaaattt | tatattttta | gaagtgatga | aagtgcgaat | 900 |
| ttaacgcagg | gctttatgta | ttttaatgtc | aatcaaacca | tacaagaagt | tgaaaatgta | 960 |
| gatcttagcg | aatttatgcg | aagaattagt | ggtagtgaaa | ttgttttttt | gttttctttg | 1020 |
| tttggttttg | tatggctttt | gagaaaacat | aaaagtatga | ttatggcttt | acctatattg | 1080 |
| gtgcttgggt | ttttagcctt | aaaaggggg | cttagattta | ccatttattc | tgtacctgta | 1140 |
| atggccttag | gatttggttt | tttattgagc | gagtttaagg | ctataatggt | taaaaaatat | 1200 |
| agccaattaa | cttcaaatgt | ttgtattgtt | tttgcaacta | ttttgacttt | agctccagta | 1260 |
| tttatccata | tttacaacta | taaagcgcca | acagttttt | ctcaaaatga | agcatcatta | 1320 |
| ttaaatcaat | taaaaaatat | agccaataga | gaagattatg | tggtaacttg | gtgggattat | 1380 |
| ggttatcctg | tgcgttatta | tagcgatgtg | aaaactttag | tagatggtgg | aaagcattta | 1440 |
| ggtaaggata | atttttccc | ttcttttgct | ttaagcaaag | atgaacaagc | tgcagctaat | 1500 |
| atggcaagac | ttagtgtaga | atatacagaa | aaaagctttt | atgctccgca | aaatgatatt | 1560 |
| ttaaaaacag | acattttgca | agccatgatg | aaagattata | atcaaagcaa | tgtggatttg | 1620 |
| tttctagctt | cattatcaaa | acctgatttt | aaaatcgata | cgccaaaaac | tcgtgatatt | 1680 |
| tatctttata | tgcccgctag | aatgtctttg | attttttcta | cggtggctag | ttttttcttt | 1740 |
| attaatttag | atacaggagt | tttggataaa | ccttttacct | ttagcacagc | ttatccactt | 1800 |
| gatgttaaaa | atggagaaat | ttatcttagc | aacggagtgg | ttttaagcga | tgattttaga | 1860 |
| agtttttaaaa | taggtgataa | tgtggtttct | gtaaatagta | tcgtagagat | taattctatt | 1920 |
| aaacaaggtg | aatacaaaat | cactccaatt | gatgataagg | ctcagtttta | tatttttat | 1980 |
| ttaaaggata | gtgctattcc | ttacgcacaa | tttattttaa | tggataaaac | catgtttaat | 2040 |

-continued

```
agtgcttatg tgcaaatgtt ttttttagga aattatgata agaatttatt tgacttggtg    2100
attaattcta gagatgctaa ggttttaaa cttaaaattt aa                        2142
```

<210> SEQ ID NO 2
<211> LENGTH: 713
<212> TYPE: PRT
<213> ORGANISM: Campylobacter jejuni

<400> SEQUENCE: 2

```
Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
290                 295                 300

Phe Met Tyr Phe Asn Val Asn Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350
```

```
Met Ile Met Ala Leu Pro Ile Leu Val Leu Gly Phe Leu Ala Leu Lys
            355                 360                 365

Gly Gly Leu Arg Phe Thr Ile Tyr Ser Val Pro Val Met Ala Leu Gly
370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
            405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
            435                 440                 445

Asn Arg Glu Asp Tyr Val Val Thr Trp Trp Asp Tyr Gly Tyr Pro Val
            450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
            515                 520                 525

Met Met Lys Asp Tyr Asn Gln Ser Asn Val Asp Leu Phe Leu Ala Ser
            530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
            595                 600                 605

Leu Ser Asn Gly Val Val Leu Ser Asp Asp Phe Arg Ser Phe Lys Ile
            610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
                660                 665                 670

Leu Met Asp Lys Thr Met Phe Asn Ser Ala Tyr Val Gln Met Phe Phe
            675                 680                 685

Leu Gly Asn Tyr Asp Lys Asn Leu Phe Asp Leu Val Ile Asn Ser Arg
            690                 695                 700

Asp Ala Lys Val Phe Lys Leu Lys Ile
705                 710

<210> SEQ ID NO 3
<211> LENGTH: 5
<212> TYPE: PRT
<213> ORGANISM: Artificial Sequence
<220> FEATURE:
<223> OTHER INFORMATION: Glycosylation site
```

```
<220> FEATURE:
<221> NAME/KEY: MISC_FEATURE
<222> LOCATION: (1)..(5)
<223> OTHER INFORMATION: Glycosylation site wherein X is any amino acid
      except proline

<400> SEQUENCE: 3

Asp Xaa Asn Xaa Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any aminoacid
      except proline

<400> SEQUENCE: 4

Asp Xaa Asn Xaa Thr
1               5

<210> SEQ ID NO 5
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any amino acid
      except proline

<400> SEQUENCE: 5

Glu Xaa Asn Xaa Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any aminoacid
      except proline

<400> SEQUENCE: 6

Glu Xaa Asn Xaa Thr
1               5

<210> SEQ ID NO 7
<211> LENGTH: 19
<212> TYPE: DNA
<213> ORGANISM: Artificial Sequence
<220> FEATURE:
<223> OTHER INFORMATION: recognition sequence

<400> SEQUENCE: 7
ctgtctcttg atcagatct                                              19
```

```
<210> SEQ ID NO 8
<211> LENGTH: 19
<212> TYPE: DNA
<213> ORGANISM: Artificial Sequence
<220> FEATURE:
<223> OTHER INFORMATION: recognition sequence

<400> SEQUENCE: 8
acttgtgtat aagagtcag                                              19

<210> SEQ ID NO 9
<211> LENGTH: 33
<212> TYPE: DNA
<213> ORGANISM: Artificial Sequence
<220> FEATURE:
<223> OTHER INFORMATION: recombination site sequence

<400> SEQUENCE: 9
ataacttcgt ataatgtatg ctatacgaag tag                              33

<210> SEQ ID NO 10
<211> LENGTH: 34
<212> TYPE: DNA
<213> ORGANISM: Artificial Sequence
<220> FEATURE:
<223> OTHER INFORMATION: recombination site sequence

<400> SEQUENCE: 10
ataacttcgt ataatgtatg ctatacgaag ttat                             34

<210> SEQ ID NO 11
<211> LENGTH: 48
<212> TYPE: DNA
<213> ORGANISM: Artificial Sequence
<220> FEATURE:
<223> OTHER INFORMATION: recognition site sequences

<400> SEQUENCE: 11
gaagttccta ttccgaagtt cctattctct agaaagtata ggaacttc              48

<210> SEQ ID NO 12
<211> LENGTH: 48
<212> TYPE: DNA
<213> ORGANISM: Artificial Sequence
<220> FEATURE:
<223> OTHER INFORMATION: recognition site sequence

<400> SEQUENCE: 12
gaagtaccta ttccgaagtt cctattctct agaaagtata ggaacttc              48

<210> SEQ ID NO 13
<211> LENGTH: 1032
<212> TYPE: DNA
<213> ORGANISM: Artificial Sequence
<220> FEATURE:
<223> OTHER INFORMATION: recombinase

<400> SEQUENCE: 13
atgtccaatt tactgaccgt acaccaaaat ttgcctgcat taccggtcga tgcaacgagt    60
gatgaggttc gcaagaacct gatggacatg ttcagggatc gccaggcgtt ttctgagcat   120
acctggaaaa tgcttctgtc cgtttgccgg tcgtgggcgg catggtgcaa gttgaataac   180
cggaaatggt ttcccgcaga acctgaagat gttcgcgatt atcttctata tcttcaggcg   240
cgcggtctgg cagtaaaaac tatccagcaa catttgggcc agctaaacat gcttcatcgt   300
```

```
cggtccgggc tgccacgacc aagtgacagc aatgctgttt cactggttat gcggcggatc    360
cgaaaagaaa acgttgatgc cggtgaacgt gcaaaacagg ctctagcgtt cgaacgcact    420
gatttcgacc aggttcgttc actcatggaa aatagcgatc gctgccagga tatacgtaat    480
ctggcatttc tggggattgc ttataacacc ctgttacgta tagccgaaat tgccaggatc    540
agggttaaag atatctcacg tactgacggt gggagaatgt taatccatat tggcagaacg    600
aaaacgctgg ttagcaccgc aggtgtgagg aaggcactta gcctggggt aactaaactg    660 gtcgagcgat ggatttccgt ctctggtgta gctgatgatc cgaataacta cctgttttgc    720
cgggtcagaa aaaatggtgt tgccgcgcca tctgccacca gccagctatc aactcgcgcc    780
ctggaaggga ttttttgaagc aactcatcga ttgatttacg gcgctaagga tgactctggt    840
cagagatacc tggcctggtc tggacacagt gcccgtgtcg gagccgcgcg agatatggcc    900
cgcgctggag tttcaatacc ggagatcatg caagctggtg gctggaccaa tgtaaatatt    960
gtcatgaact atatccgtaa cctggatagt gaaacagggg caatggtgcg cctgctggaa   1020
gatggcgatt ag                                                       1032

<210> SEQ ID NO 14
<211> LENGTH: 1272
<212> TYPE: DNA
<213> ORGANISM: Artificial Sequence
<220> FEATURE:
<223> OTHER INFORMATION: recombinase FLP FRT system

<400> SEQUENCE: 14
atgagccagt tcgatatcct gtgtaaaacc ccgcctaagg tgcttgttcg tcagtttgtg     60
gaaaggtttg aaagaccttc aggtgagaaa atagcatcct gtgctgctga actaacctat    120
ttatgttgga tgattacaca taacggaaca gcaatcaaga gagccacatt catgagctat    180
aatactatca taagcaattc gctgagtttc gatattgtca ataaatcact ccagttaaa     240 tacaagacgc aaaaagcaac aattctggaa gcctcattaa agaaattgat tcctgcttgg    300
gaatttacaa ttattcctta caacggacaa aaacatcaat ctgatatcac tgatattgta    360
agtagtttgc aattacagtt cgaatcatcg gaagaagcag ataagggaaa tagccacagt    420
aaaaaaatgc ttaaagcact tctaagtgag ggtgaaagca tctgggagat cactgagaaa    480
atactaaatt cgtttgagta tacttcgaga tttacaaaaa caaaaacttt ataccaattc    540
ctcttcctag ctactttcat caattgtgga agattcagcg atattaagaa cgttgatccg    600
aaatcattta aattagtcca aaataagtat ctggggagtaa taatccagtg tttagtgaca    660
gagacaaaga caagcgttag taggcacata tacttcttta gcgcaagggg taggatcgat    720
ccacttgtat atttggatga attttttgagg aattctgaac cagtcctaaa acgagtaaat    780
aggaccggca attcttcaag caataaacag gaataccaat tattaaaaga taacttagtc    840
agatcgtaca ataaagcttt gaagaaaaat gcgccttatc cgatctttgc tataaaaat    900 ggcccaaaat ctcacattgg aagacatttg atgacctcat ttctttcaat gaagggccta    960
acggagttga ctaatgttgt gggaaattgg agcgataagc gtgcttctgc cgtggccagg   1020
acaacgtata ctcatcagat aacagcaata cctgatcact acttcgcact agtttctcgg   1080
tactatgcat atgatccaat atcaaggaa atgatagcat tgaaggatga gactaatcca   1140
attgaggagt ggcagcatat agaacagcta aagggtagtg ctgaaggaag catacgatac   1200
cccgcatgga atgggataat atcacaggag gtactagact acctttcatc ctacataaat   1260
agacgcatat ag                                                       1272
```

```
<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
ttttgcggcc gcttctacgt gttccgcttc c                                  31

<210> SEQ ID NO 16
<211> LENGTH: 31
<212> TYPE: DNA
<213> ORGANISM: Artificial Sequence
<220> FEATURE:
<223> OTHER INFORMATION: primer

<400> SEQUENCE: 16
ttttgcggcc gcattgcgtt gcgctcactg c                                  31

<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17
ttttgcggcc gcttctcatg tttgacagct tatc                               34

<210> SEQ ID NO 18
<211> LENGTH: 31
<212> TYPE: DNA
<213> ORGANISM: Artificial Sequence
<220> FEATURE:
<223> OTHER INFORMATION: primer

<400> SEQUENCE: 18
ttttgcggcc gcagcgagtc agtgagcgag g                                  31

<210> SEQ ID NO 19
<211> LENGTH: 34
<212> TYPE: DNA
<213> ORGANISM: Artificial Sequence
<220> FEATURE:
<223> OTHER INFORMATION: primer

<400> SEQUENCE: 19
ttttgcgatc gcttctcatg tttgacagct tatc                               34

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
ttttaggcct agcgagtcag tgagcgagg                                     29

<210> SEQ ID NO 21
<211> LENGTH: 603
<212> TYPE: DNA
<213> ORGANISM: Artificial Sequence
<220> FEATURE:
<223> OTHER INFORMATION: pJCUSA1
```

<400> SEQUENCE: 21

```
ggccgcctag gccgcggccg cctacttcgt atagcataca ttatacgaag ttatgtctga    60
cgctcagtgg aacgacgcgt aactcacgtt aagggatttt ggtcatgatc agcacgttga   120
caattaatca tcggcatagt atatcggcat agtataatac gacaaggtga ggaactaaaa   180
catggccaag ttgaccagtg ccgttccggt gctcaccgcg cgcgacgtcg ccggagcggt   240
cgagttctgg accgaccggc tcgggttctc ccgggacttc gtggaggacg acttcgccgg   300
tgtggtccgg gacgacgtga ccctgttcat cagcgcggtc caggaccagg tggtgccgga   360
caacaccctg gcctgggtgt gggtgcgcgg cctggacgag ctgtacgccg agtggtcgga   420
ggtcgtgtcc acgaacttcc gggacgcctc cgggccggcc atgaccgaga tcggcgagca   480
gccgtggggg cgggagttcg ccctgcgcga cccggccggc aactgcgtgc acttcgtggc   540
cgaggagcag gactgaataa cttcgtatag catacattat acgaagttat ggccgcctag   600
gcc                                                                 603
```

<210> SEQ ID NO 22
<211> LENGTH: 2133
<212> TYPE: DNA
<213> ORGANISM: Campylobacter sputorum

<400> SEQUENCE: 22

```
atgtcaaatt ttaatttcgc taaatttcta aataaattac ctagactttc taaacatact    60
attttaatga ttgttttagc tgtttgtttt gggatatttt gcagatttta ctgggtagtt   120
tgggctagtg cttatccgca tttttatatgg aatgatcagc ttatgataag cacaaatgac   180
ggatatgcat ttgctgaggg cacaagagat atgatagctg ttttcatca accaaacgat   240
ctttcttact atggctcatc tctttcgacg cttagcatgt ggttatataa cattttgcca   300
ttttcattag aaactatact tttgtatatg agtacatttt tatctccact cttagctgtg   360
cctttgatac ttataggtaa agaactaaac gcttcaaaag cgggttttat agctgcactt   420
ctagctatta ttgcaaatag ttattataat agaacaatga gtggatatta cgatacggat   480
atgctaaata tcactcttcc tatgatggtt ttttggagca taacaagact tgttcaaaga   540
aaagagagag taaatttaat atttattccg gttttatgg cgatatatgg atggtggtat   600
ccatcttctt actcactatt acttgccatg attggaatgt ttttttttata taccattgtt   660
tttgaaagat acgaaaaact aaactatgaa gctatggttt ttatgatttt agcaatcaca   720
agcttttcta tacaaattaa atttattata gttattgttt tgtatgcttt aatctatttt   780
taccaaagat ttttttgataa aaaagtaata tttgcattaa ttatggcttc gttaatatgc   840
tttatatggc ttggcgggct aaaccctata cttttttaaca ttaaattta tatatttaga   900
gacattgcag atagcggtga tgctgttttt aaatttttca atgtaaatca acaataaga   960
gaaagttctg cgatagattt taacacagtt gtaactagga ttagcgggca tttaatagta  1020
ttttttggtat ctattatagg atatatttta tttataaaaa acaataaaat tttactacta  1080
actttaccga ttctgttttt gggtcttatg tcatttaaaa gtggtttaag atttacaata  1140
tactcagttc cagtaatggc tcttggtttt ggctattttg ttatgtattg ttttgcaaaa  1200
atagatataa aagatcgttt tttaggttat gtgttttat ttgttgtaac atttagtgca  1260
ttatatccat ctttaaaaca tatttatgat tataaagtat ttcctgtttt tacacatagc  1320
gaagttgaaa gtttgataa tttaaaaaat attgcaaaaa gagaagatta tgtgctttct  1380
tggtgggatt atggttatcc gatcagatat tattcagatg taaaaactct catagatgga  1440
```

```
ggaaaacatc ttggaagtga taacttcgcc gttagctttg cacttggaag cgatcaaaat    1500
agctctgcaa atatggcaag attagaagtt gaatatacag aaaaaaatta tgaagaaaaa    1560
tttggattaa atttaaaaaa gatgatgaaa gattataatg ctacaaatgt taatgagttt    1620
ttattatcat taaagatgaa aaatttaact ctgccaaagc aaacaagaga tatttattac    1680
tatttaccag atagaatgat atacatatat ccgatagtgc tagattttc tagacttgat     1740 ttgacaacag ggcaagaatt tgcccagccg ttttttatgg ttagtgagag attttcagct    1800
acaaatgata atcaaataat gttaaataac aatgtcatat taagtaatga tggcactaaa    1860
ttatcgataa atggcaactc ttatagtgta aatacatatg ttgaaacaag ttatgatcaa    1920
aacgaaaaat taaatgtaaa ttattttaac atagatccaa atagcaattt ttatgtgatt    1980
tttatgaaag attatttgag aattttggtt ttagataaaa ctttgtatga tagtgcgtat    2040
attcaacttt ttgtattaga aaattatgat aaaaatttat ttgaaccagt gattttaaac    2100
ggatcaacta aaatttataa actcaaaaaa tga                                2133
```

<210> SEQ ID NO 23
<211> LENGTH: 710
<212> TYPE: PRT
<213> ORGANISM: campylobacter sputorum

<400> SEQUENCE: 23

```
Met Ser Asn Phe Asn Phe Ala Lys Phe Leu Asn Lys Leu Pro Arg Leu
1               5                   10                  15

Ser Lys His Thr Ile Leu Met Ile Val Leu Ala Val Cys Phe Gly Ile
            20                  25                  30

Phe Cys Arg Phe Tyr Trp Val Val Trp Ala Ser Ala Tyr Pro His Phe
        35                  40                  45

Ile Trp Asn Asp Gln Leu Met Ile Ser Thr Asn Asp Gly Tyr Ala Phe
    50                  55                  60

Ala Glu Gly Thr Arg Asp Met Ile Ala Gly Phe His Gln Pro Asn Asp
65                  70                  75                  80

Leu Ser Tyr Tyr Gly Ser Ser Leu Ser Thr Leu Ser Met Trp Leu Tyr
                85                  90                  95

Asn Ile Leu Pro Phe Ser Leu Glu Thr Ile Leu Leu Tyr Met Ser Thr
            100                 105                 110

Phe Leu Ser Pro Leu Leu Ala Val Pro Leu Ile Leu Ile Gly Lys Glu
        115                 120                 125

Leu Asn Ala Ser Lys Ala Gly Phe Ile Ala Ala Leu Leu Ala Ile Ile
    130                 135                 140

Ala Asn Ser Tyr Tyr Asn Arg Thr Met Ser Gly Tyr Tyr Asp Thr Asp
145                 150                 155                 160

Met Leu Asn Ile Thr Leu Pro Met Met Val Phe Trp Ser Ile Thr Arg
                165                 170                 175

Leu Val Gln Arg Lys Glu Arg Val Asn Leu Ile Phe Ile Pro Val Phe
            180                 185                 190

Met Ala Ile Tyr Gly Trp Trp Tyr Pro Ser Ser Tyr Ser Leu Leu Leu
        195                 200                 205

Ala Met Ile Gly Met Phe Phe Leu Tyr Thr Ile Val Phe Glu Arg Tyr
    210                 215                 220

Glu Lys Leu Asn Tyr Glu Ala Met Val Phe Met Ile Leu Ala Ile Thr
225                 230                 235                 240

Ser Phe Ser Ile Gln Ile Lys Phe Ile Ile Val Ile Val Leu Tyr Ala
                245                 250                 255
```

-continued

```
Leu Ile Tyr Phe Tyr Gln Arg Phe Phe Asp Lys Lys Val Ile Phe Ala
            260                 265                 270

Leu Ile Met Ala Ser Leu Ile Cys Phe Ile Trp Leu Gly Gly Leu Asn
        275                 280                 285

Pro Ile Leu Phe Asn Ile Lys Phe Tyr Ile Phe Arg Asp Ile Ala Asp
    290                 295                 300

Ser Gly Asp Ala Val Phe Lys Phe Phe Asn Val Asn Gln Thr Ile Arg
305                 310                 315                 320

Glu Ser Ser Ala Ile Asp Phe Asn Thr Val Thr Arg Ile Ser Gly
                325                 330                 335

His Leu Ile Val Phe Leu Val Ser Ile Ile Gly Tyr Ile Leu Phe Ile
            340                 345                 350

Lys Asn Asn Lys Ile Leu Leu Leu Thr Leu Pro Ile Leu Phe Leu Gly
                355                 360                 365

Leu Met Ser Phe Lys Ser Gly Leu Arg Phe Thr Ile Tyr Ser Val Pro
        370                 375                 380

Val Met Ala Leu Gly Phe Gly Tyr Phe Val Met Tyr Cys Phe Ala Lys
385                 390                 395                 400

Ile Asp Ile Lys Asp Arg Phe Leu Gly Tyr Val Phe Leu Phe Val Val
                405                 410                 415

Thr Phe Ser Ala Leu Tyr Pro Ser Leu Lys His Ile Tyr Asp Tyr Lys
            420                 425                 430

Val Phe Pro Val Phe Thr His Ser Glu Val Glu Ser Leu Asp Asn Leu
        435                 440                 445

Lys Asn Ile Ala Lys Arg Glu Asp Tyr Val Leu Ser Trp Trp Asp Tyr
    450                 455                 460

Gly Tyr Pro Ile Arg Tyr Tyr Ser Asp Val Lys Thr Leu Ile Asp Gly
465                 470                 475                 480

Gly Lys His Leu Gly Ser Asp Asn Phe Ala Val Ser Phe Ala Leu Gly
                485                 490                 495

Ser Asp Gln Asn Ser Ser Ala Asn Met Ala Arg Leu Glu Val Glu Tyr
            500                 505                 510

Thr Glu Lys Asn Tyr Glu Glu Lys Phe Gly Leu Asn Leu Lys Lys Met
        515                 520                 525

Met Lys Asp Tyr Asn Ala Thr Asn Val Asn Glu Phe Leu Leu Ser Leu
    530                 535                 540

Lys Asp Glu Asn Leu Thr Leu Pro Lys Gln Thr Arg Asp Ile Tyr Tyr
545                 550                 555                 560

Tyr Leu Pro Asp Arg Met Ile Tyr Ile Tyr Pro Ile Val Leu Asp Phe
                565                 570                 575

Ser Arg Leu Asp Leu Thr Thr Gly Gln Glu Phe Ala Gln Pro Phe Phe
            580                 585                 590

Met Val Ser Glu Arg Phe Ser Ala Thr Asn Asp Asn Gln Ile Met Leu
        595                 600                 605

Asn Asn Asn Val Ile Leu Ser Asn Asp Gly Thr Lys Leu Ser Ile Asn
    610                 615                 620

Gly Asn Ser Tyr Ser Val Asn Thr Tyr Val Glu Thr Ser Tyr Asp Gln
625                 630                 635                 640

Asn Glu Lys Leu Asn Val Asn Tyr Phe Asn Ile Asp Pro Asn Ser Asn
                645                 650                 655

Phe Tyr Val Ile Phe Met Lys Asp Tyr Leu Arg Ile Leu Val Leu Asp
            660                 665                 670
```

```
Lys Thr Leu Tyr Asp Ser Ala Tyr Ile Gln Leu Phe Val Leu Glu Asn
        675                 680                 685

Tyr Asp Lys Asn Leu Phe Glu Pro Val Ile Leu Asn Gly Ser Thr Lys
    690                 695                 700

Ile Tyr Lys Leu Lys Lys
705             710

<210> SEQ ID NO 24
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 24

Asp Val Asn Val Thr
1               5

<210> SEQ ID NO 25
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 25

Glu Val Asn Ala Thr
1               5

<210> SEQ ID NO 26
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 26

Asp Gln Asn Ala Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 27

Asp Asn Asn Asn Thr
1               5

<210> SEQ ID NO 28
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 28

Asp Asn Asn Asn Ser
1               5

<210> SEQ ID NO 29
<211> LENGTH: 5
<212> TYPE: PRT
<213> ORGANISM: Artificial Sequence
```

```
<220> FEATURE:
<223> OTHER INFORMATION: Amino Acid Motif

<400> SEQUENCE: 29

Asp Gln Asn Arg Thr
1               5

<210> SEQ ID NO 30
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 30

Glu Asn Asn Phe Thr
1               5

<210> SEQ ID NO 31
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 31

Asp Ser Asn Ser Thr
1               5

<210> SEQ ID NO 32
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 32

Asp Gln Asn Ile Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 33

Asp Gln Asn Val Ser
1               5

<210> SEQ ID NO 34
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 34

Asp Asn Asn Val Ser
1               5

<210> SEQ ID NO 35
<211> LENGTH: 5
<212> TYPE: PRT
<213> ORGANISM: Artificial Sequence
```

<220> FEATURE:
<223> OTHER INFORMATION: Amino Acid Motif

<400> SEQUENCE: 35

Asp Tyr Asn Val Ser
1               5

<210> SEQ ID NO 36
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 36

Asp Phe Asn Val Ser
1               5

<210> SEQ ID NO 37
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 37

Asp Phe Asn Ala Ser
1               5

<210> SEQ ID NO 38
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 38

Asp Phe Asn Ser Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 39

Asp Val Asn Ala Thr
1               5

<210> SEQ ID NO 40
<211> LENGTH: 5
<212> TYPE: PRT
<213> ORGANISM: Artificial Sequence
<220> FEATURE:
<223> OTHER INFORMATION: Amino Acid Motif

<400> SEQUENCE: 40

Asp Phe Asn Val Thr
1               5

<210> SEQ ID NO 41
<211> LENGTH: 5
<212> TYPE: PRT
<213> ORGANISM: Artificial Sequence

```
<220> FEATURE:
<223> OTHER INFORMATION: Amino Acid Motif

<400> SEQUENCE: 41

Asp Val Asn Ala Ser
1               5
```